(12) United States Patent
El Alaoui et al.

(10) Patent No.: US 11,376,333 B2
(45) Date of Patent: Jul. 5, 2022

(54) MTG SUBSTRATES FOR COVALENT CONJUGATION OF COMPOUNDS

(71) Applicant: COVALAB, Villeurbanne (FR)

(72) Inventors: Saïd El Alaoui, Saint Bonnet de Mure (FR); Vincent Thomas, Villeurbanne (FR)

(73) Assignee: COVALAB, Villeurbanne (FR)

( * ) Notice: Subject to any disclaimer, the term of this patent is extended or adjusted under 35 U.S.C. 154(b) by 943 days.

(21) Appl. No.: 15/104,892

(22) PCT Filed: Dec. 23, 2014

(86) PCT No.: PCT/EP2014/079278
§ 371 (c)(1),
(2) Date: Jun. 15, 2016

(87) PCT Pub. No.: WO2015/097267
PCT Pub. Date: Jul. 2, 2015

(65) Prior Publication Data
US 2016/0361434 A1 Dec. 15, 2016

(30) Foreign Application Priority Data

Dec. 23, 2013 (EP) .................................... 13306847
Apr. 14, 2014 (EP) .................................... 14305548

(51) Int. Cl.
| | | |
|---|---|---|
| *A61K 47/65* | (2017.01) | |
| *C07K 7/06* | (2006.01) | |
| *C07K 7/08* | (2006.01) | |
| *C07K 16/00* | (2006.01) | |
| *A61K 47/68* | (2017.01) | |

(52) U.S. Cl.
CPC .......... *A61K 47/65* (2017.08); *A61K 47/6889* (2017.08); *C07K 7/06* (2013.01); *C07K 7/08* (2013.01); *C07K 16/00* (2013.01); *C07K 2319/00* (2013.01)

(58) Field of Classification Search
CPC .......... A61K 47/48338; A61K 47/6889; A61K 47/65; C07K 7/06; C07K 7/09; C07K 16/00; C07K 2319/00
See application file for complete search history.

(56) References Cited

U.S. PATENT DOCUMENTS

| | | | |
|---|---|---|---|
| 5,270,163 A | 12/1993 | Gold et al. | |
| 2003/0027999 A1* | 2/2003 | Rosen | A61P 37/04 536/23.1 |
| 2007/0092926 A1* | 4/2007 | Alterman | C07K 16/40 435/23 |
| 2008/0108795 A1* | 5/2008 | Guo | C07K 16/2863 530/387.7 |
| 2008/0234183 A1* | 9/2008 | Hallbrink | A61K 51/0448 514/1.1 |
| 2013/0121983 A1* | 5/2013 | Jones | C07K 16/2803 424/94.5 |
| 2013/0230543 A1* | 9/2013 | Pons | C07K 16/30 424/178.1 |

FOREIGN PATENT DOCUMENTS

| | | | | |
|---|---|---|---|---|
| EP | 0322094 B1 | * | 12/1992 | .......... C07K 14/765 |
| JP | 2007-197434 A | | 8/2007 | |
| WO | 00/43492 A2 | | 7/2000 | |
| WO | 2010/037395 A2 | | 4/2010 | |
| WO | 2012/059882 A2 | | 5/2012 | |
| WO | 2013/092983 A2 | | 6/2013 | |

OTHER PUBLICATIONS

Kamiya et al., Enzyme and Microbial Tech., 33 (2003) 492-496.*
Ahmed et al., scFv Antibody: Principles and Clinical Application, Clinical and Developmental Immunology, vol. 2012, Article ID 980250, 15 pages.*
Beck et al., Discov Med. Oct. 2010;10(53):329-39.*
Sugimura et al., JI Biol. Chem. vol. 281, No. 26, pp. 17699-17706, 2006 (Year: 2006).*
Salanoubat et al. Putative uncharacterized protein At3g56140; version 44, 2011 [online database][retrieved May 4, 2020] Retrieved from https://www.uniprot.org/uniprot. (Year: 2011).*
Tenascin-X of Stylophora pistillata protein sequence reference [online database][retrieved May 4, 2020] Retrieved from NCBI, Genbank Seq ID: PFX31894.1. (Year: 2017).*
Brad Stuart, The Hospice Journal (The Haworth Press, Inc.) vol. 14, No. 3/4, 1999 pp. 139-154 (Year: 1999).*
C. Gapalan, The National Medical Journal of India, vol. 5, No. 3, 145-151 (1992, first published 1968) (Year: 1992).*
Lartigue, OncologyLive, 2012, vol. 13, issue 6, 8 pages (Year: 2012).*
Kamiya et al. "New Fluorescent Substrates of Microbial Transglutaminase and its Application to Peptide Tag-Directed Covalent Protein Labeling". Methods in Molecular Biology, vol. 751, 81-94, 2011.
Abe et al. "Enzymatic Single-Step Preparation of Multifunctional Proteins" ChemComm, vol. 46, 7160-7162, 2010.
Mindt et al. "Modification of Different IgG1 Antibodies via Glutamine and Lysine using Bacterial and Human Tissue Transglutaminase". Biconjucate Chemistry, vol. 19, 271-278, 2008.
Tominaga et al. "Design of a Specific Peptide Tage that Affords Covalent and Site-Specific Enzyme Immobilization Catalyzed by Microbial Transglutaminase". Biomacromolecules, vol. 6, No. 4, 2299-2304, 2005.
Takazawa et al. "Enzymatic Labeling of a Single Chain Variable Fragment of an Antibody With Alkaline Phosphatase by Microbial Transglutaminase", Biotechnology and Bioengineering, pp. 399-404, vol. 86, No. 4, 2004.

(Continued)

*Primary Examiner* — Fred H Reynolds
*Assistant Examiner* — Joseph Fischer
(74) *Attorney, Agent, or Firm* — Oliff PLC

(57) ABSTRACT

The present invention relates to a substrate for transglutaminase comprising a peptide having from 3 to 15 amino acids and comprising the amino acid sequence $X_{-4}X_{-3}X_{-2}X_{-1}QX_{+1}X_{+2}X_{+3}X_{+4}$, bound to a first molecule.

9 Claims, 10 Drawing Sheets

Specification includes a Sequence Listing.

(56) References Cited

OTHER PUBLICATIONS

Strop et al. "Location Matters: Site of Conjugation Modulates Stability and Pharmacokinetics of Antibody Drug Conjugates", Chemistry & Biology, vol. 20, pp. 161-167, 2013.
Lin et al. "Transglutaminase-Catalyzed Site-Specific Conjugation of Small-Molecule Probes to Proteins in Vitro and on the Surface of Living Cells", Journal of The American Chemical Society, vol. 128, No. 14, 4542-4543, 2006.
Kamiya et al. "Site-Specific Cross-Linking of Functional Proteins by Transglutamination", Enzyme and Microbial Technology, vol. 33, No. 4, 492-496, 2003.
Mar. 12, 2015 International Search Report issued in International Patent Application No. PCT/EP2014/079278.
Sugimura et al.,"Screening for the Preferred Substrate Sequence of Transglutaminase Using a Phage-Displayed Peptide Library",J. Biol. Chem., Jun. 30, 2006, vol. 281, No. 26.
Stamnaes et al.,"The Propensity for Deamidation and Transamidation of Peptides by Transglutaminase 2 Is Dependent on Substrate Affinity and Reaction Conditions", Biochimica et biophysica acta, Aug. 28, 2008.

\* cited by examiner

SEQUENCE LISTING

<160> NUMBER OF SEQ ID NOS: 33

<210> SEQ ID NO 1
<211> LENGTH: 6
<212> TYPE: PRT
<213> ORGANISM: Artificial Sequence
<220> FEATURE:
<223> OTHER INFORMATION: Peptide DH6Q5

<400> SEQUENCE: 1

Asp Val Tyr Ser Gln His
1               5

<210> SEQ ID NO 2
<211> LENGTH: 5
<212> TYPE: PRT
<213> ORGANISM: Artificial Sequence
<220> FEATURE:
<223> OTHER INFORMATION: Peptide FE5Q4

<400> SEQUENCE: 2

Phe Trp Ile Gln Glu
1               5

<210> SEQ ID NO 3
<211> LENGTH: 6
<212> TYPE: PRT
<213> ORGANISM: Artificial Sequence
<220> FEATURE:
<223> OTHER INFORMATION: Peptide PH6Q4

<400> SEQUENCE: 3

Pro Leu Val Gln Ser His
1               5

<210> SEQ ID NO 4
<211> LENGTH: 6
<212> TYPE: PRT
<213> ORGANISM: Artificial Sequence
<220> FEATURE:
<223> OTHER INFORMATION: Peptide PS6Q3

<400> SEQUENCE: 4

Pro Ser Val Gln Glu Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Peptide PY7Q5

<400> SEQUENCE: 5

Pro Leu Lys His Gln Glu Tyr
1               5

<210> SEQ ID NO 6
<211> LENGTH: 12
<212> TYPE: PRT
<213> ORGANISM: Artificial Sequence
<220> FEATURE:
<223> OTHER INFORMATION: Peptide HH12Q11

<400> SEQUENCE: 6

His Asp Leu Met Trp Pro Asp Val Tyr Ser Gln His
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Peptide WH8Q7

<400> SEQUENCE: 7

Trp Pro Asp Val Tyr Ser Gln His
1               5

<210> SEQ ID NO 8
<211> LENGTH: 8
<212> TYPE: PRT
<213> ORGANISM: Artificial Sequence
<220> FEATURE:
<223> OTHER INFORMATION: Peptide SY10Q8

```
<400> SEQUENCE: 8

Ser Pro Leu Lys His Gln Glu Tyr
1               5

<210> SEQ ID NO 9
<211> LENGTH: 12
<212> TYPE: PRT
<213> ORGANISM: Artificial Sequence
<220> FEATURE:
<223> OTHER INFORMATION: Peptide GS12Q7

<400> SEQUENCE: 9

Gly Gly Ser Pro Leu Ala Gln Ser His Gly Gly Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Peptide HH12N11

<400> SEQUENCE: 10

His Asp Leu Met Trp Pro Asp Val Tyr Ser Asn His
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Peptide HG14Q11

<400> SEQUENCE: 11

His Asp Leu Met Trp Pro Asp Val Tyr Ser Gln His Gly Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Peptide WG10Q7

<400> SEQUENCE: 12

Trp Pro Asp Val Tyr Ser Gln His Gly Gly
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Peptide DH6N5

<400> SEQUENCE: 13

Asp Val Tyr Ser Asn His
1               5

<210> SEQ ID NO 14
<211> LENGTH: 13
<212> TYPE: PRT
<213> ORGANISM: Artificial Sequence
<220> FEATURE:
<223> OTHER INFORMATION: Peptide CF13Q4

<400> SEQUENCE: 14
```

```
Cys Tyr Glu Gln His Lys Leu Pro Ser Ser Trp Pro Phe
1               5                   10
```

```
<210> SEQ ID NO 15
<211> LENGTH: 9
<212> TYPE: PRT
<213> ORGANISM: Artificial Sequence
<220> FEATURE:
<223> OTHER INFORMATION: Peptide CS9Q4

<400> SEQUENCE: 15

Cys Tyr Glu Gln His Lys Leu Pro Ser
1               5
```

```
<210> SEQ ID NO 16
<211> LENGTH: 12
<212> TYPE: PRT
<213> ORGANISM: Artificial Sequence
<220> FEATURE:
<223> OTHER INFORMATION: Peptide FY12Q10

<400> SEQUENCE: 16

Phe Pro Trp Ser Ser Pro Leu Lys His Gln Glu Tyr
1               5                   10
```

```
<210> SEQ ID NO 17
<211> LENGTH: 8
<212> TYPE: PRT
<213> ORGANISM: Artificial Sequence
<220> FEATURE:
<223> OTHER INFORMATION: Peptide CW8Q3

<400> SEQUENCE: 17

Cys Asp Gln Met Met Leu Pro Trp
1               5
```

```
<210> SEQ ID NO 18
<211> LENGTH: 10
<212> TYPE: PRT
<213> ORGANISM: Artificial Sequence
<220> FEATURE:
<223> OTHER INFORMATION: Peptide YV10

<400> SEQUENCE: 18

Tyr Leu Ala Asp Thr Asn Ser Leu Ala Val
1               5                   10
```

```
<210> SEQ ID NO 19
<211> LENGTH: 6
<212> TYPE: PRT
<213> ORGANISM: Artificial Sequence
<220> FEATURE:
<223> OTHER INFORMATION: Peptide CV6Q3

<400> SEQUENCE: 19

Cys His Gln Ser Tyr Val
1               5
```

```
<210> SEQ ID NO 20
<211> LENGTH: 6
<212> TYPE: PRT
<213> ORGANISM: Artificial Sequence
<220> FEATURE:
<223> OTHER INFORMATION: Peptide PH6Q4

<400> SEQUENCE: 20
```

Pro Leu Val Gln Ser His
1               5

<210> SEQ ID NO 21
<211> LENGTH: 7
<212> TYPE: PRT
<213> ORGANISM: Artificial Sequence
<220> FEATURE:
<223> OTHER INFORMATION: Peptide VF7Q5

<400> SEQUENCE: 21

Val Trp Arg Ser Gln Tyr Phe
1               5

<210> SEQ ID NO 22
<211> LENGTH: 6
<212> TYPE: PRT
<213> ORGANISM: Artificial Sequence
<220> FEATURE:
<223> OTHER INFORMATION: Peptide DE6Q5

<400> SEQUENCE: 22

Asp Val Tyr Ser Gln Glu
1               5

<210> SEQ ID NO 23
<211> LENGTH: 7
<212> TYPE: PRT
<213> ORGANISM: Artificial Sequence
<220> FEATURE:
<223> OTHER INFORMATION: Peptide HL8Q6

<400> SEQUENCE: 23

His Asn Lys Ser Gln Ala Leu
1               5

<210> SEQ ID NO 24
<211> LENGTH: 11
<212> TYPE: PRT
<213> ORGANISM: Artificial Sequence
<220> FEATURE:
<223> OTHER INFORMATION: Peptide LN11Q8-10

<400> SEQUENCE: 24

Leu Leu Thr Leu Pro Ser Val Gln Glu Gln Asn
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Peptide LN11Q10

<400> SEQUENCE: 25

Leu Leu Thr Leu Pro Ser Val Ser Glu Gln Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Peptide KL7Q5

<400> SEQUENCE: 26

Lys Glu Glu Phe Gln Pro Leu

```
1               5

<210> SEQ ID NO 27
<211> LENGTH: 8
<212> TYPE: PRT
<213> ORGANISM: Artificial Sequence
<220> FEATURE:
<223> OTHER INFORMATION: Peptide SY8Q6

<400> SEQUENCE: 27

Ser Pro Leu Lys His Gln Glu Tyr
1               5

<210> SEQ ID NO 28
<211> LENGTH: 7
<212> TYPE: PRT
<213> ORGANISM: Artificial Sequence
<220> FEATURE:
<223> OTHER INFORMATION: Peptide WD7Q7

<400> SEQUENCE: 28

Trp Pro Leu Met Met Gln Asp
1               5

<210> SEQ ID NO 29
<211> LENGTH: 5
<212> TYPE: PRT
<213> ORGANISM: Artificial Sequence
<220> FEATURE:
<223> OTHER INFORMATION: synthetic peptide

<400> SEQUENCE: 29

Tyr Glu Ile Gln Arg
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic peptide

<400> SEQUENCE: 30

Tyr Glu Ala Gln Lys
1               5

<210> SEQ ID NO 31
<211> LENGTH: 5
<212> TYPE: PRT
<213> ORGANISM: Artificial Sequence
<220> FEATURE:
<223> OTHER INFORMATION: synthetic peptide

<400> SEQUENCE: 31

Tyr Glu Ala Gln Arg
1               5

<210> SEQ ID NO 32
<211> LENGTH: 5
<212> TYPE: PRT
<213> ORGANISM: Artificial Sequence
<220> FEATURE:
<223> OTHER INFORMATION: synthetic peptide

<400> SEQUENCE: 32

Trp Pro Ala Gln Arg
1               5
```

```
<210> SEQ ID NO 33
<211> LENGTH: 5
<212> TYPE: PRT
<213> ORGANISM: Artificial Sequence
<220> FEATURE:
<223> OTHER INFORMATION: synthetic peptide

<400> SEQUENCE: 33

Tyr Glu Val Gln Lys
1               5
```

MTG SUBSTRATES FOR COVALENT CONJUGATION OF COMPOUNDS

FIELD OF THE INVENTION

The present invention relates to peptides which selectively and specifically react as glutamine donors with transglutaminase.

The present invention also relates to substrates for transglutaminase comprising these peptides bound to a first molecule and uses thereof.

BACKGROUND OF THE INVENTION

Covalent bonds formation between proteins and various functional small molecules (e.g., fluorophore, ligands) as well as macromolecules (e.g., proteins, polymers, nucleic acids) has represented an important molecular basis for creating protein conjugates employed in biotechnology and biomedical applications. Such linkage between a protein and a functional molecule must not affect the biological function of the protein.

In order to minimize the effect of the linkage of a functional molecule on the biological function of target proteins, enzymatic routes appear to be an intriguing option.

Harnessing the catalytic properties of enzymes is a field of research that continues to receive increasing attention. Transglutaminases (TGases) have always attracted a wide interest from both scientific and applied research due to their capacity to cross-link protein substrates with high regio- and stereo-selectivity TGases (EC 2.3.2.13) are widely distributed family of enzymes that catalyze post-translational protein cross-linking through the formation of a relatively protease-resistant isopeptide bonds. The key step for catalysis involves the interaction of a -carboxamide group of a glutamine (Gln) residue of a polypeptide substrate with the TGase's active site, forming a reactive thioacyl-moiety at the level of a Cys residue and then reaction with an amino donor, thus leading to a new isopeptide amide bond (FOLK J E, COLE P W. J Biol Chem. 1965 July; 240:2951-60).

The earliest biocatalytic use of TGases was in the food industry (Zhu, Y.; Rinzema, A.; Tramper, J. Appl.Microbiol. Biotechnol. 1995, 44, 277-282).$_1$ Novel biotechnological applications have since expanded the use of TGases outside of food field.

Kamiya et al. have reported the potential utility of TGase in covalent protein labelling (New fluorescent substrates of microbial transglutaminase and its application to peptide tag-directed covalent protein labelling, Kamiya N, Abe H., Methods Mol Biol. 2011; 751:81-94 and Enzymatic single-step preparation of multifunctional proteins, Abe H, Goto M, Kamiya N., Chem Commun (Camb). 2010 Oct. 14; 46(38): 7160-2).

In WO2013/092983, it is also disclosed methods of functionalization of immunoglobulins in particular with drugs using TGase. This approach, describes the method to obtain new site by directed mutagenesis to generate a Q-donor inside the heavy chain of the antibody. This empiric method needs to test high number of mutants as the rules which govern selection by TGases of glutamine residues for modification are still largely unknown. Consequently, using this method to develop new antibodies bearing Q-donor is time consuming and cost effective.

WO2012/059882 further discloses specific engineered polypeptide conjugates and methods of making such conjugates using transglutaminases.

One difficulty in using TGase for covalent linking between a protein and a functional molecule is to design a functional first substrate which can be used as a general linker with a good incorporation rate without modifying the function or activity of said first substrate.

Furthermore, once the functional molecule has been linked with the protein, both first protein and second molecule must keep their function or activity.

SUMMARY OF THE INVENTION

The Applicant has found peptides which, when generated or bound to a first molecule, are particularly efficient and specific substrate for transglutaminase.

The substrates for transglutaminase comprising the peptides found by the applicant bound to a first molecule exhibit a high rate of covalent linkage between this substrate and a second molecule.

The rate of covalent linkage has been shown to be high for a large variety of first molecule even for molecule known to be difficult to efficiently link with a second molecule (e.g. immunoglobulin, molecule immobilized on a solid support).

Further to the ability to easily link a first and a second molecule, the use of such peptides for transglutamination allows both first and second molecules to maintain their original functional properties.

The present invention therefore relates to a substrate for transglutaminase comprising:
a peptide having from 3 to 15 amino acids and comprising the amino acid sequence $X_{-4}X_{-3}X_{-2}X_{-1}QX_{+1}X_{+2}X_{+3}X_{+4}$, wherein:
$X_{-4}$ is absent or is any amino acid, preferably a negatively charged amino acid or a non-polar amino acid,
$X_{-3}$ is absent or is an amino acid selected from the group consisting of an aromatic, a non-polar hydrophobic and a non-polar amino acid,
$X_{-2}$ is absent or is any amino acid, preferably selected from the group consisting of negatively charged or non-polar amino acids,
$X_{-1}$ is an amino acid selected from the group consisting of a polar neutral, a positively charged, a non-polar amino acid, and a non-polar hydrophobic amino acid,
Q is glutamine,
$X_{+1}$ is an amino acid selected from the group consisting of a polar neutral, a positively charged, a non-polar hydrophobic, and a negatively charged amino acid,
$X_{+2}$ is absent or is an amino acid selected from the group consisting of a polar neutral, an aromatic, a non-polar hydrophobic and a positively charged amino acid,
$X_{+3}$ is absent or is any amino acid, preferably a non-polar amino acid and
$X_{+4}$ is absent or is any amino acid,
wherein said peptide is bound to a first molecule.

In specific embodiment, the substrates according to the invention may comprise the above peptide, wherein, either,
(i) $X_{-1}$ is serine and $X_{+1}$ is histidine, tyrosine, alanine or glutamic acid;
(ii) $X_{-1}$ is alanine or valine, and $X_{+1}$ is lysine, arginine or alanine, wherein, when $X_{-1}$ is alanine, $X_{+1}$ is lysine or arginine; or,
(iii) $X_{-1}$ is isoleucine and $X_{+1}$ is arginine, lysine or glutamic acid.

The present invention also relates to a conjugated compound comprising the substrate for transglutaminase of the invention covalently bound to a second molecule comprising at least an alkylamine or a lysine.

The present invention also relates to the conjugated compound of the invention, wherein the first molecule is an antibody and the second molecule is a drug, for use in a method of treatment of human or animal body.

The present invention also relates to a method for covalently binding the substrate for transglutaminase of the invention to a second molecule comprising at least an alkylamine or a lysine residue comprising the step of reacting the substrate for transglutaminase with the second molecule in the presence of a transglutaminase.

The present invention also relates to a peptide having from 3 to 15 amino acids and comprising the amino acid sequence $X_{-4}X_{-3}X_{-2}X_{-1}QX_{+1} X_{+2}X_{+3}X_{+4}$, wherein:
  $X_{-4}$ is absent or is any amino acid, preferably a negatively charged amino acid or a non-polar amino acid,
  $X_{-3}$ is absent or is an amino acid selected from the group consisting of an aromatic, a non-polar hydrophobic and a non-polar amino acid,
  $X_{-2}$ is absent or is any amino acid, preferably selected from the group consisting of negatively charged or non-polar amino acids,
  $X_{-1}$ is an amino acid selected from the group consisting of a polar neutral, a positively charged, a non-polar amino acid, and a non-polar hydrophobic amino acid,
  Q is glutamine,
  $X_{+1}$ is an amino acid selected from the group consisting of a polar neutral, a positively charged, a non-polar hydrophobic, and a negatively charged amino acid,
  $X_{+2}$ is absent or is any amino acid, preferably selected from the group consisting of a polar neutral, an aromatic, a non-polar hydrophobic and a positively charged amino acid,
  $X_{+3}$ is absent or is any amino acid, preferably a non-polar amino acid and
  $X_{+4}$ is absent or is any amino acid.

The present invention also relates to the use of the peptide of the invention as a linker for covalent coupling of molecules.

The present invention also relates to a method for covalently binding a first molecule to a second molecule comprising at least an alkylamine or a lysine comprising the steps of:
  binding the first molecule to a peptide of the invention to obtain a substrate for transglutaminase,
  reacting the substrate for transglutaminase with the second molecule in the presence of a transglutaminase, preferably bacterial transglutaminase, for example *Streptoverticillium mobaraense* transglutaminase (mTG).

The present invention also relates to a fusion protein, comprising a peptide of the invention fused to a polypeptide.

The present invention also relates to a kit for labeling a molecule comprising at least a lysine or an alkylamine comprising the substrate of the invention wherein the first molecule is a reporter group.

The present invention also relates to a method for labeling a molecule comprising at least an alkylamine or a lysine comprising the step of reacting the substrate of the invention wherein the first molecule is a reporter group with the molecule to label in the presence of a transglutaminase.

DETAILED DESCRIPTION OF THE INVENTION

Definitions

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding portion that immunospecifically binds an antigen. As such, the term antibody encompasses not only whole antibody molecules, but also antibody fragments, including antigen-binding fragments or portions, as well as variants (including derivatives) of antibodies and antibody fragments. In conventional antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding portion, therefore, includes six CDRs, comprising the CDR set from each of a heavy and a light chain V region. Framework Regions (FRs) refer to amino acid sequences interposed between CDRs.

Examples of binding fragments encompassed within the term "antigen-binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., 1989 Nature 341:544-546), which consists of a VH domain; and an isolated complementarity determining region (CDR), or any fusion proteins comprising such antigen-binding portion.

As used therein, residues of antibodies are numbered according to Kabat scheme.

The term "human antibody" refers to an antibody in which a substantial portion of the antibody molecule resembles, in amino acid sequence or structure, that of an antibody derived from human origin.

A "human antibody" may be considered more suitable in instances where it is desirable to reduce the immunogenicity of the antibody for administration to humans for therapeutic purposes.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH:VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. an antibody according to the invention) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "subject" denotes a mammal, such as a rodent, a feline, a canine, and a primate. Preferably a subject according to the invention is a human.

"Treatment or treating" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the subject to be treated herein may have been diagnosed as having the disorder or may be predisposed or susceptible to the disorder.

As used herein, the term "alkylamine" refers to a group of the formula-NHR" (monoalkylamine) where R" is an alkyl or a group of the formula-NR"R" (dialkyl amine), where each R" is independently an alkyl.

As used herein, the term "aptamer" refers to single-stranded or double-stranded oligo-DNA, oligo-RNA or oligo-DNA/RNA or any analogue thereof that can specifically bind to a target molecule such as a protein or peptide, more typically to a peptide. Advantageously, aptamers can display fairly high specificity and affinity (e.g., K[A] in the order $1 \times 10^9$ $M^{-1}$) for their targets. Aptamer production is described, inter alia, in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated specifically by reference herein.

Peptides of the Invention

The present invention relates to a peptide having from 3 to 15 amino acids and comprising the amino acid sequence $X_{-4}X_{-3}X_{-2}X_{-1}QX_{+1}X_{+2}X_{+3}X_{+4}$, wherein:

$X_{-4}$ is absent or is any amino acid, preferably a negatively charged amino acid or a non-polar amino acid, $X_{-3}$ is absent or is an amino acid selected from the group consisting of an aromatic, a non-polar hydrophobic and a non-polar amino acid, $X_{-2}$ is absent or is any amino acid, preferably selected from the group consisting of negatively charged or non-polar amino acids, $X_{-1}$ is an amino acid selected from the group consisting of a polar neutral, a positively charged, a non-polar amino acid, and a non-polar hydrophobic amino acid, Q is glutamine, $X_{+1}$ is an amino acid selected from the group consisting of a polar neutral, a positively charged, a non-polar hydrophobic, and a negatively charged amino acid, $X_{+2}$ is absent or is any amino acid, preferably selected from the group consisting of a polar neutral, an aromatic, a non-polar hydrophobic and a positively charged amino acid, $X_{+3}$ is absent or is any amino acid, preferably a non-polar amino acid and $X_{+4}$ is absent or is any amino acid.

Typically, the peptide of the invention has 3, 4, 5 6, 7, 8, 9, 10, 11, 12, 13, 14 or 15 amino acids.

Preferably, the peptide has 4, 5, 6, 7, 8, 9, 10, 11 or 12 amino acids.

As used herein, the term "negatively charged amino acids" preferably refer to the following amino acids: Glutamic acid (E) and aspartic acid (D).

As used herein, the term "aromatic amino acids" preferably refer to the following amino acids: Tyrosine (Y), tryptophan (W) and phenylalanine (F).

As used herein, the term "non-polar amino acids" preferably refer to the following amino acids: Isoleucine (I), proline (P) and Cysteine (C).

As used herein, the term "positively charged amino acids" preferably refer to the following amino acids: Histidine (H), Lysine (K).

As used herein, the term "non-polar hydrophobic amino acids" preferably refer to the following amino acids: Leucine (L), Alanine (A) and Valine (V).

As used herein, the term "polar neutral amino acids" preferably refer to the following amino acids: Serine (S), and glutamine (Q).

In a specific embodiment, the peptide comprises the amino acid sequence $X_{-4}X_{-3}X_{-2-1}QX_{+1}X_{+2}X_{+3}X_{+4}$, wherein:
- $X_{-4}$ is absent or is any amino acid, preferably an aspartic acid or a proline,
- $X_{-3}$ is absent or is an amino acid selected from the group consisting of tyrosine, tryptophane, phenylalanine, proline, valine and leucine,
- $X_{-2}$ is absent or is an amino acid selected from the group consisting of glutamic acid, proline, tyrosine, tryptophan, lysine, cysteine, leucine, histidine and serine,
- $X_{-1}$ is an amino acid selected from the group consisting of serine, histidine, isoleucine, valine and alanine,
- Q is glutamine,
- $X_{+1}$ is an amino acid selected from the group consisting of arginine, lysine, histidine, glutamic acid, serine and alanine,
- $X_{+2}$ is absent or is any amino acid, preferably selected from the group consisting of histidine, tyrosine, lysine, glutamine, leucine and serine,
- $X_{+3}$ is absent or is any amino acid, preferably proline, and
- $X_{+4}$ is absent or is any amino acid.

In a specific embodiment, X−3 is tyrosine or tryptophane.

In another specific embodiment, X−2 is glutamic acid or proline.

In a preferred embodiment, $X_{-1}$ is a serine, an alanine, a valine, a histidine or an isoleucine. In another specific embodiment, $X_{-1}$ is a serine, an alanine or an isoleucine. In another specific embodiment, X−1 is isoleucine, alanine or valine.

In a preferred embodiment, $X_{+1}$ is an histidine, a glutamic acid or a serine. More preferably $X_{+1}$ is a serine. In another preferred embodiment, $X_{+1}$ is a lysine or an arginine.

In related preferred embodiments, $X_{+1}$ is a lysine or an arginine, and $X_{-1}$ is an alanine or an isoleucine.

In a preferred embodiment, X−3 is tyrosine or tryptophane, X−2 is glutamic acid or proline, X−1 is isoleucine, alanine or valine, $X_{+1}$ is a lysine or an arginine.

In other preferred embodiments,
(i) $X_{-1}$ is serine and $X_{+1}$ is histidine, tyrosine, alanine or glutamic acid;
(ii) $X_{-1}$ is alanine or valine, and $X_{+1}$ is lysine, arginine or alanine, wherein, when $X_{-1}$ is alanine, $X_{+1}$ is lysine or arginine; or,
(iii) $X_{-1}$ is isoleucine and $X_{+1}$ is arginine, lysine or glutamic acid.

In a preferred embodiment, the peptide comprises the amino acid sequence selected from the group consisting of SEQ ID NO: 29, SEQ ID NO: 30, SEQ ID NO: 31, SEQ ID NO: 32 and SEQ ID NO:33.

The amino acid sequences are given in table 1 below.

TABLE 1

| Name | SEQ ID NO: | Amino acid sequence |
|---|---|---|
| DH6Q5 | 1 | DVYSQH |
| FE5Q4 | 2 | FWIQE |
| PH6Q4 | 20 | PLVQSH |
| PS6Q3 | 4 | PSVQES |
| PY7Q5 | 5 | PLKHQEY |
| HH12Q11 | 66 | HDLMWPDVYSQH |
| WH8Q7 | 7 | WPDVYSQH |
| SY10Q8 | 8 | SPLKHQEY |
| BEST1 | 29 | YEIQR |
| BEST2 | 30 | YEAQK |
| BEST3 | 31 | YEAQR |
| BEST4 | 32 | WPAQR |
| BEST5 | 33 | YEVQK |

In a preferred embodiment, the peptide has the amino acid sequence selected from the group consisting of SEQ ID NO: 1, SEQ ID NO: 2, SEQ ID NO: 20, SEQ ID NO: 4, SEQ ID NO: 5, SEQ ID NO: 6, SEQ ID NO: 7, SEQ ID NO:8, SEQ ID NO:29, SEQ ID NO:30, SEQ ID NO:31, SEQ ID NO: 32 and SEQ ID NO:33.

The present invention also relates to the use of the peptide of the invention as a linker for covalent coupling of molecules.

The present invention also relates to the use of the peptide of the invention as a linker for covalent coupling of protein or antibody to a second molecule, wherein the second molecule is selected from the group consisting of a protein, an antibody, a drug, a nucleic acid, a radioactive element, a reporter group, a stabilizing molecule and a molecule immobilized on a solid support.

The present invention also relates to a method for covalently binding a first molecule to a second molecule comprising at least an alkylamine residue or a lysine comprising the steps of:
- binding the first molecule to a peptide of the invention to obtain a substrate for transglutaminase,
- reacting the substrate for transglutaminase with the second molecule in the presence of a transglutaminase.

Glutamine-Donor Substrate for Transglutaminase of the Invention

The present invention relates to a substrate for transglutaminase, more specifically, Q-donor substrates, comprising:
a peptide having from 3 to 15 amino acids and comprising the amino acid sequence $X_{-4}X_{-3}X_{-2}X_{-1}QX_{+1}X_{+2}X_{+3}X_{+4}$, wherein:
- $X_{-4}$ is absent or is any amino acid, preferably a negatively charged amino acid or a non-polar amino acid,
- $X_{-3}$ is absent or is an amino acid selected from the group consisting of an aromatic, a non-polar hydrophobic and a non-polar amino acid,
- $X_{-2}$ is absent or is any amino acid, preferably selected from the group consisting of negatively charged or a non-polar amino acid,
- $X_{-1}$ is an amino acid selected from the group consisting of a polar neutral, a positively charged, a non-polar amino acid, and a non-polar hydrophobic amino acid, Q is glutamine, $X_{+1}$ is an amino acid selected from the group consisting of a polar neutral, a positively charged, a non-polar hydrophobic, and a negatively charged amino acid, $X_{+2}$ is absent or is any amino acid, preferably selected from the group consisting of a polar neutral, an aromatic, a non-polar hydrophobic and a positively charged amino acid, $X_{+3}$ is absent or is any amino acid, preferably a non-polar amino acid and $X_{+4}$ is absent or is any amino acid.

bound to: —a first molecule.

Transglutaminase (TGase) may be for example a tissue transglutaminase (TG2) (Gentile V., Saydak M., Chiocca E. A., Akande O., Birckbichler P. J., Lee K. N., Stein J. P., Davies P. J. A. J. Biol. Chem. 266:478-483(1991) or a microbial transglutaminase (mTG) (Ando H, Adachi M, Umeda K, Matsuura A, Nonaka M, Uchio R, Tanaka H, Motoki M. Agric Biol Chem 1989; 53:2613-2617).

Preferably, the transglutaminase is a microbial transglutaminase, for example transglutaminase from *Streptoverticillium mobaraense*.

Typically, the peptide of the invention for use in the Q-donor substrates, has 3, 4, 5 6, 7, 8, 9, 10, 11, 12, 13, 14 or 15 amino acids.

Preferably, the peptide for use in the Q-donor substrates has 4, 5, 6, 7, 8, 9, or 10 amino acids.

In a preferred embodiment, the peptide for use in the Q-donor substrates comprises the amino acid sequence $X_{-4}X_{-3}X_{-2}X_{-1}QX_{+1}X_{+2}X_{+3}X_{+4}$, wherein:

$X_{-4}$ is absent or is any amino acid, preferably an aspartic acid or a proline, $X_{-3}$ is absent or is an amino acid selected from the group consisting of phenylalanine, proline, valine, tyrosine, tryptophane and leucine, $X_{-2}$ is absent or is an amino acid selected from the group consisting of glutamic acid, proline, tyrosine, tryptophan, lysine, cysteine, leucine, histidine and serine, $X_{-1}$ is an amino acid selected from the group consisting of serine, histidine, isoleucine, valine and alanine, Q is glutamine, $X_{+1}$ is an amino acid selected from the group consisting of lysine arginine, histidine, glutamic acid, serine and alanine, $X_{+2}$ is absent or is any amino acid, and preferably selected from the group consisting of histidine, tyrosine, lysine, glutamine, leucine and serine, $X_{+3}$ is absent or is any amino acid, preferably proline, and $X_{+4}$ is absent or is any amino acid.

In a specific embodiment, X-3 is tyrosine or tryptophane.

In another specific embodiment, X-2 is glutamic acid or proline.

In a preferred embodiment, $X_{-1}$ is a serine, an alanine, a valine, a histidine or an isoleucine. In another specific embodiment, $X_{-1}$ is a serine, an alanine or an isoleucine. In another specific embodiment, X-1 is isoleucine, alanine or valine.

In a preferred embodiment, $X_{+1}$ is an histidine, a glutamic acid or a serine. More preferably $X+_1$ is a serine. In another preferred embodiment, $X_{+1}$ is a lysine or an arginine.

In related preferred embodiments, $X_{+1}$ is a lysine or an arginine, and $X_{-1}$ is an alanine or an isoleucine.

In a preferred embodiment, X-3 is tyrosine or tryptophane, X-2 is glutamic acid or proline, X-1 is isoleucine, alanine or valine, $X_{+1}$ is a lysine or an arginine.

In a preferred embodiment, either (i) $X_{-1}$ is serine and $X_{+1}$ is histidine, tyrosine, alanine or glutamic acid;

(ii) $X_{-1}$ is alanine or valine, and $X_{+1}$ is lysine, arginine or alanine, wherein, when $X_{-1}$ is alanine, $X_{+1}$ is lysine or arginine; or, (iii) $X_{-1}$ is isoleucine and $X_{-1}$ is arginine, lysine or glutamic acid.

In a preferred embodiment, the peptide for use in Q-donor substrate, has the amino acid sequence selected from the group consisting of SEQ ID NO: 1, SEQ ID NO: 2, SEQ ID NO: 20, SEQ ID NO: 4, SEQ ID NO: 5, SEQ ID NO: 6, SEQ ID NO: 7, SEQ ID NO: 8, SEQ ID NO:29, SEQ ID NO:30, SEQ ID NO:31, SEQ ID NO:32 and SEQ ID NO:33.

In a preferred embodiment, the peptide for use in Q-donor substrate, comprises the amino acid sequence selected from the group consisting of SEQ ID NO:29, SEQ ID NO:30, SEQ ID NO:31, SEQ ID NO:32, and SEQ ID NO:33.

In a preferred embodiment, the first molecule is selected from the group consisting of a protein, an antibody, a drug, a nucleic acid, a radioactive element, a reporter group, a stabilizing molecule, an aptamer, a ribozyme, a domain antibody, a nanobody, a non immunoglobulin scaffold, a vector particle and a molecule immobilized on a solid support.

Nucleic acids may be for example, DNA, RNA or SiRNA.

Vector particles may be, for example, nanoparticles, vesicles, viral vector particles or virus like particles.

Radioactive elements may be, for example, radioiodide or radioisotopes.

Reporter groups may be, for example, radioactive labeled compounds, fluorescent compounds such as isothiocyanate (e.g. FITC or TRITC), succinimidyl esters (e.g. NHS-fluorescein), maleimide activated fluorophores (e.g. fluorescein-5-maleimide), an enzyme such as peroxidase, an affinity peptide tag or compounds which may be detected by NMR or ESR spectroscopy.

Stabilizing molecules may be, for example, polymers such as PEG.

Non immunoglobulin scaffolds may be, for example, adnectins, ankyrins, lipocalins, affilins, protein epitope mimetics and the like.

Drug may be peptides and polypeptides, relatively large chemical entities, negatively charged chemical entities and/or hydrophobic chemical entities.

Drug is preferably a cytotoxic drug. Cytotoxic drugs may be for example duocarmycins, maytansanoids, alkylating agents, taxanes, MMAE, MMAF.

In a more preferred embodiment, the first molecule is an antibody.

The peptide for use in Q-donor substrate, is bound to the first molecule.

As used herein, the term "bound" refers to binding that may be covalent, e.g., by chemically coupling, or non-covalent, e.g., ionic interactions, hydrophobic interactions, hydrogen bonds, etc.

Covalent bonds can be, for example, ester, ether, phosphoester, amide, peptide, imide, carbon-sulfur bonds, carbon-phosphorus bonds, and the like. The term also includes the enclosement, or partial enclosement, of a substance. The term "bound" is broader than and includes terms such as "coupled", "fused", "enclosed", "packaged", "pseudotyped", "expressed in a lipid bilayer" and "attached."

In a preferred embodiment, the peptide is covalently bound to the first molecule.

In a preferred embodiment, the first molecule is a polypeptide and the peptide is fused to the first molecule.

As used herein, the term "fusion" or "fused" refers to the combination of amino acid sequences of different origin in one polypeptide chain by in-frame combination of their coding nucleotide sequences. It must be noted that more than one nucleotide sequence may encode one given amino acid sequence due to the degeneracy of the genetic code. The term "fusion" explicitly encompasses internal fusions, (i.e. insertion of sequences of different origin within a polypeptide chain, in addition to fusion to one of its termini).

Therefore, in one embodiment, the present invention also relates to a fusion protein, comprising the peptide of the invention fused to a polypeptide.

In one embodiment of the fusion protein, the polypeptide is a heavy or light chain polypeptide of an antibody, or their antigen-binding portion, including for example polypeptide comprising VH or VL domain.

In a preferred embodiment of the fusion protein, heavy and/or light chains of the antibody are fused to the peptide of the invention, C-terminally or N-terminally. In related specific embodiments of the fusion protein, heavy and/or light chains are fused C-terminally to a peptide selected from the group consisting of SEQ ID NO:7, SEQ ID NO:29, SEQ ID NO:30, SEQ ID NO:31, SEQ ID NO:32 and SEQ ID NO:33.

In one embodiment, the fusion protein is further conjugated to a second molecule comprising at least an alkylamino residue or a lysine.

The present invention also relates to a method for covalently binding the substrate for transglutaminase of the invention to a second molecule comprising at least an alkylamine residue or a lysine comprising the step of reacting the substrate for transglutaminase with the second molecule in the presence of a transglutaminase.

The present invention also relates to a kit for labeling a molecule comprising at least a lysine or an alkylamine residue comprising the substrate for transglutaminase of the invention wherein the first molecule is a reporter group.

The present invention also relates to a method for labeling a molecule comprising at least a lysine or an alkylamine residue comprising the step of reacting the substrate for transglutaminase of the invention wherein the first molecule is a reporter group with the molecule to label in the presence of a transglutaminase.

Conjugated Compound of the Invention

The present invention also relates to a conjugated compound comprising the substrate for transglutaminase of the invention covalently bound to a second molecule comprising at least a lysine or an alkylamine residue.

Such conjugated compounds are easy to produce by TG-mediated reaction. Further, the first and the second molecule both maintain their specific functional properties. For example, in the case of an antibody comprising the peptide fused to its Fc fragment, the conjugated antibody maintains antigen-binding properties.

In a preferred embodiment, the second molecule is selected from the group consisting of a protein, an antibody, a drug, a nucleic acid, a radioactive element, a reporter group, a stabilizing molecule, an aptamer, a ribozyme, a domain antibody, a nanobody, a non immunoglobulin scaffold, a vector particle and a molecule immobilized on a solid support.

Vector particles may be, for example, nanoparticles, vesicles or viral vector particles, virus like particles.

Nucleic acids may be for example, DNA, RNA or SiRNA.

Radioactive elements may be, for example, radioiodide or radioisotopes. Reporter groups may be, for example, radioactive labeled compounds, fluorescent compounds such as isothiocyanate (e.g. FITC or TRITC), succinimidyl esters (e.g. NHS-fluorescein), maleimide activated fluorophores (e.g. fluorescein-5-maleimide), an enzyme such as peroxidase, an affinity peptide tag or compounds which may be detected by NMR or ESR spectroscopy.

Stabilizing molecules may be, for example, polymers such as PEG.

Non immunoglobulin scaffolds may be, for example, adnectins, ankyrins, lipocalins, affilins, protein epitope mimetics and the like.

Drug may be peptides and polypeptides, relatively large chemical entities, negatively charged chemical entities and/or hydrophobic chemical entities.

Drug is preferably a cytotoxic drug.

Cytotoxic drugs may be for example duocarmycins, maytansanoids, alkylating agents, taxanes, monomethylauristatin-E (MMAE), monomethylauristatin-F (MMAF).

In a preferred embodiment, the second molecule is a drug, preferably a cytotoxic drug.

In a more preferred embodiment, the first molecule is an antibody and the second molecule is a drug, preferably a cytotoxic drug.

Antibody conjugated to cytotoxic agent are promising therapeutic compounds. However, they are particularly difficult to produce. The method of the invention allows producing them easily.

The present invention relates to a pharmaceutical composition comprising a conjugated compound of the invention and a pharmaceutically acceptable carrier.

The present invention also relates to the conjugated compound of the invention for use in a method of treatment of human or animal body.

The present invention also relates to a method for the treatment of a pathologic condition or disorder in a subject in need thereof comprising administering to said subject an effective amount of the conjugated compound of the invention.

The present invention also relates a use of the conjugated compound of the invention for the preparation of a medicament.

The invention will be further illustrated by the following figures and examples. However, these examples and figures should not be interpreted in any way as limiting the scope of the present invention.

FIGURES

Peptides inhibitors were added in C: HH12Q11.

Figure 5:
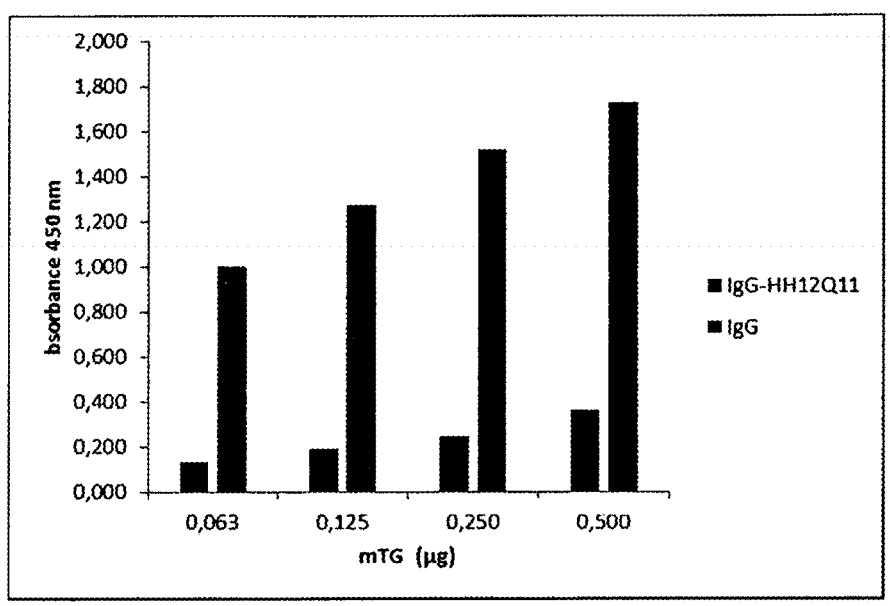

FIG. 5 shows the measurement of the incorporation of biot-cad into adsorbed IgG-HH12Q11 conjugate and free IgG control. Experimental conditions are described in B-1-3, B-I-4 and B-II-2.

Figure 6:
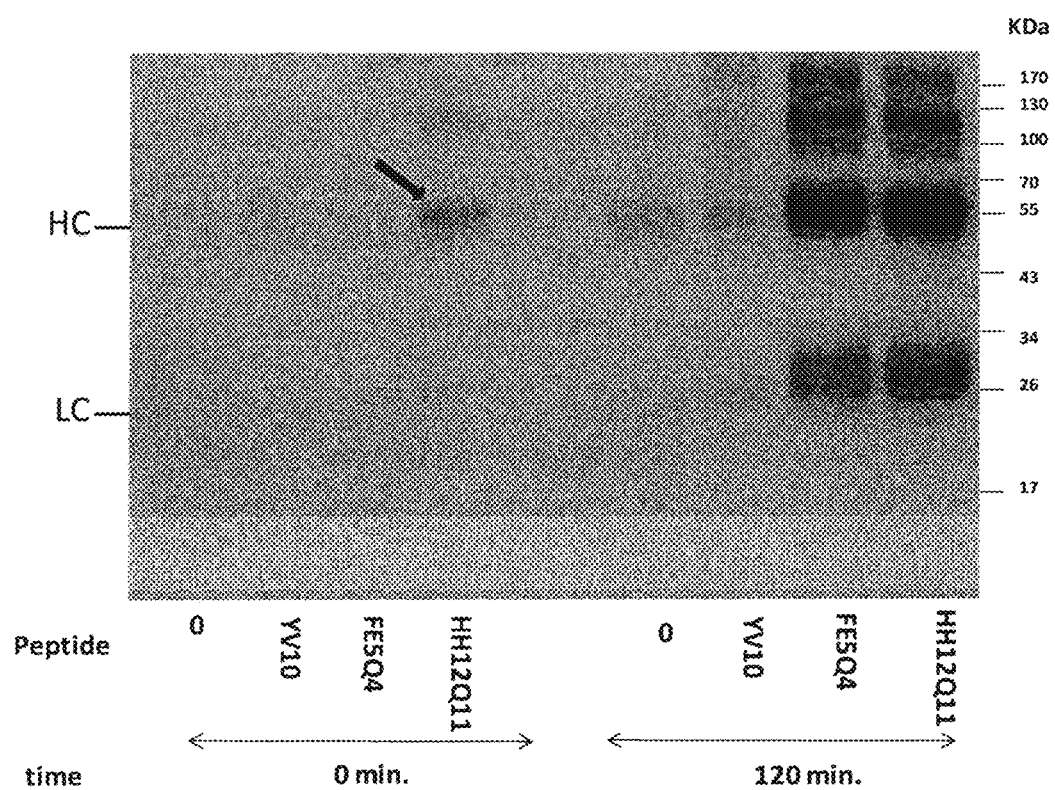

FIG. 6 shows the analysis by western blot of the incorporation of biot-cad by mTG into free IgG and peptide conjugated IgG. The enzymatic incorporation of amine substrate was incubated 2 hrs at room temperature in Tris buffer pH8 as described in B-II-5. The position of IgG heavy chain (HC) and light chain (LC) are indicated.

Figure 7A:
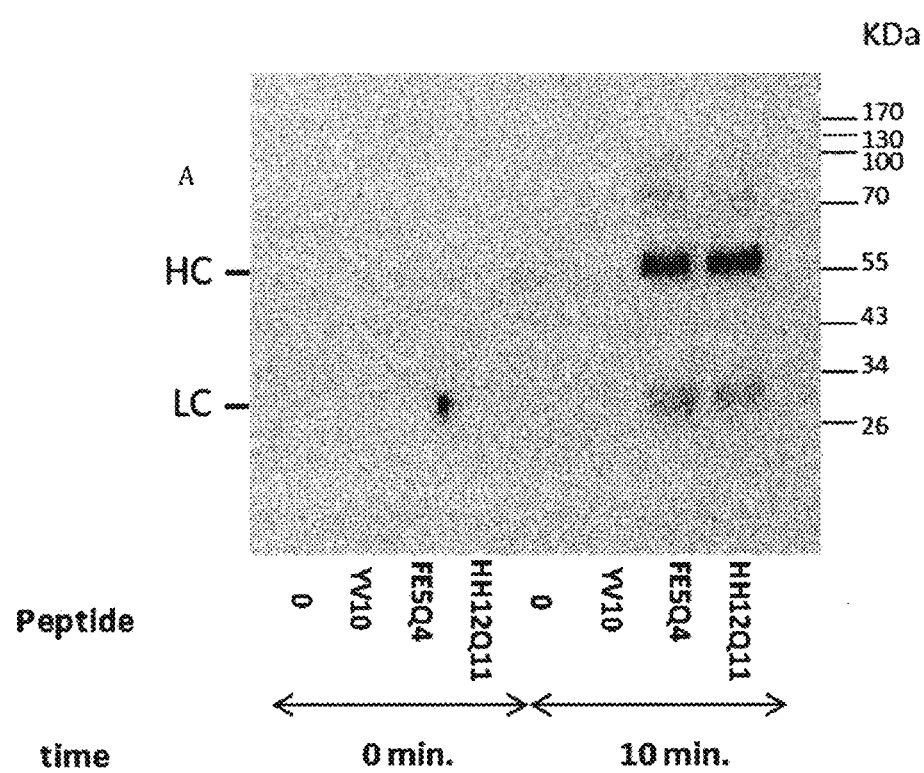
Figure 7B:
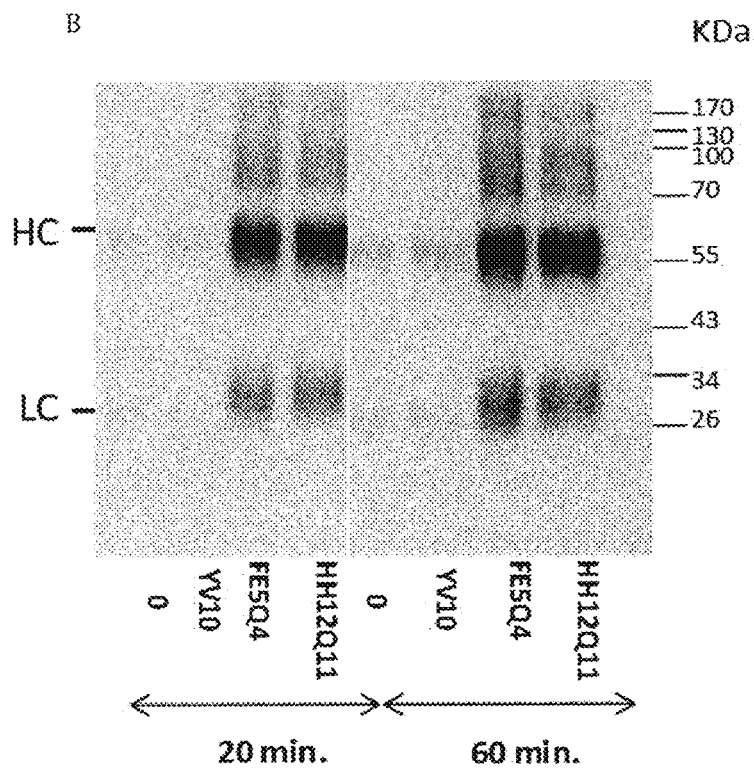

FIG. 7 shows the western blot analysis of the Kinetic study of biot-cad incorporation on peptide conjugated IgG and free IgG. mTG was incubated for the catalytic reaction at room temperature in Tris buffer pH 8 at indicated reaction time. The position of IgG heavy chain (HC) and light chain (LC) are indicated.

Figure 8:
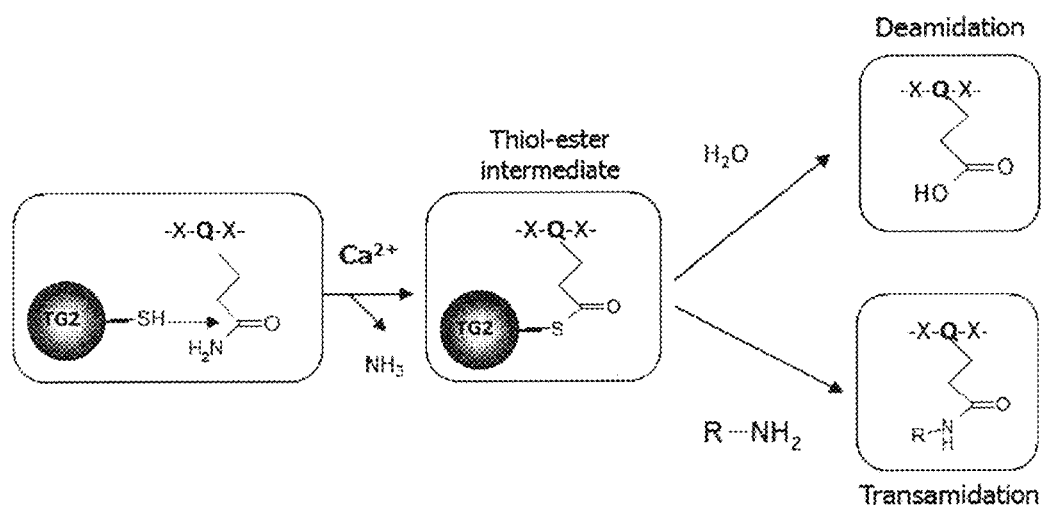

FIG. 8 is a scheme of the reaction catalyzed by a transglutaminase.

Figure 9:
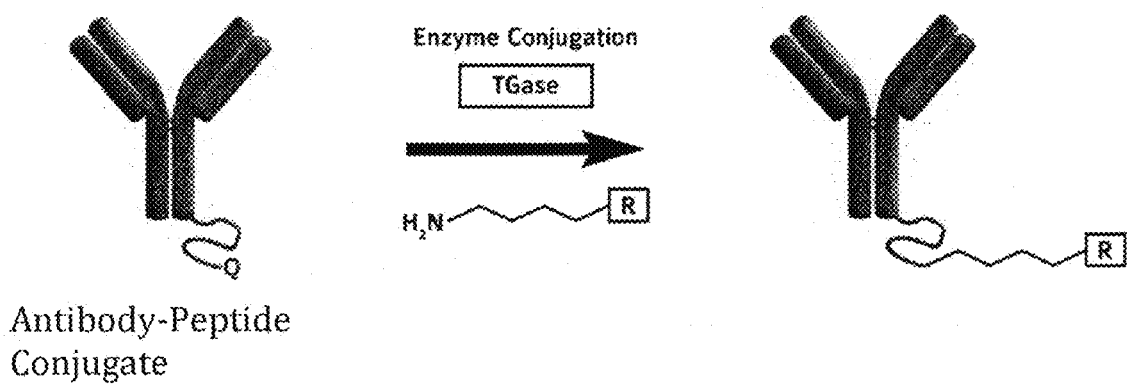

FIG. 9 is a scheme of the covalent bond formation between a substrate for transglutaminase and a second molecule.

Figure 10:
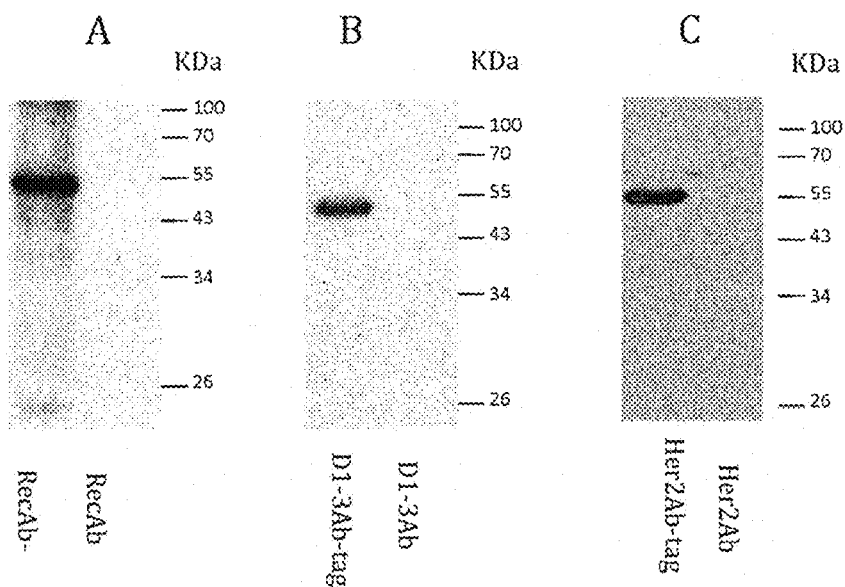

FIG. 10: Biotin-x-cadaverine incorporation by mTG on (A) RecAb, (B) D1-3 and (C) Her2Ab. Non tagged corresponding antibodies were used for the control of the specificity of mTG crosslinking FIG. 11: Kinetic of biotin-x-cadaverine incorporation by mTG on D1-3-tag antibody.

FIG. 12: Control by ELISA of the immunoreactivity of tagged recombinant antibodies in comparison with their non-tagged corresponding antibodies. (A) anti-lysozyme antibodies, (B &C) anti-her2 antibodies. In A&B anti human IgGAM-HRP antibody was used and in C streptavidin-HRP was used.

EXAMPLES

Material and Methods

A) Materials and Reagents

Bovine serum albumin (ref. A7906), human IgG (ref. I4506), glutaraldehyde (ref. G6257), spermine (spm) (ref.S2876), sodium borohydrid (ref.21,346-2), N-(3-Dimethylaminopropyl)-N'-ethyl carbodiimide hydrochloride (EDAC)(ref.E 7750), N-hydroxysuccinimide (NHS) (ref. 13,0672), dialysis tubing cellulose membrane, flat width 10 mm (ref.D9277) and Acrylamide/Bis-acrylamide, 30% solution (ref.A3574), were purchased to Sigma Aldrich, France. Nitrocellulose membrane Hybond™-C Extra Amersham (ref.RPN203E) was furnished by Dutcher, France. Microtiter plate High binding (Costar ref. 3590) are from Corning Inc, France. Recombinante microbial transglutaminase (mTG) (ref.opr 0054), recombinante human transglutaminase 2 (hTG2) (ref. opr 0027), biotine-X-cadaverine (ref.opr0007), horse radish peroxydase labeled streptavidine (opr 0011), Covabtest amine plate (ref. opr 0004), TMB-RTU (ref. opr 0052) were furnished by Covalab, France. All the peptides used were synthesized by Covalab, France. The sequence and the purity of the peptides were controled by HPLC (Water-France) and Mass spectrophotometer.

TABLE 2

List of some of the peptides screened for mTG and TG2 preferred substrates.

| Peptide number | Peptide Ref | Peptide sequence | SEQ ID NO |
|---|---|---|---|
| 1 | TGpan | Z-Q-G | |
| 2 | GS12Q7 | GGSPLAQSHGGS | 9 |
| 3 | HH12Q11 | HDLMWPDVYSQH | 6 |
| 4 | HH12N11 | HDLMWPDVYSNH | 10 |
| 5 | HG14Q11 | HDLMWPDVYSQHGG | 11 |
| 6 | WG10Q7 | WPDVYSQHGG | 12 |
| 7 | DH6Q5 | DVYSQH | 1 |
| 8 | DH6N5 | DVYSNH | 13 |
| 9 | CF13Q4 | CYEQHKLPSSWPF | 14 |
| 10 | CS9Q4 | CYEQHKLPS | 15 |
| 11 | FY12Q10 | FPWSSPLKHQEY | 16 |
| 12 | SY10Q8 | SPLKHQEY | 8 |
| 13 | CW8Q3 | CDQMMLPW | 17 |
| 14 | FE5Q4 | FWIQE | 2 |
| 15 | YV10 | YLADTNSLAV | 18 |

Q donor is in bold and underlined. In some peptides Q was replaced by N.

B) Methods

B-I-Methods for Preparation of Conjugated Substrates

B-I-1: Preparation of Covalently Coupling Peptides to 96 Well-Microtiter Plates (Covabtest-Peptide)

The coupling method was previously described by the Applicant (V. Thomas et al, 2004) and also in the corresponding data sheet of CovAbtest-Plate™ which is commercially available from Covalab (Ref #opr0004). Briefly, in separate tubes a solution mixture containing 150 µM of each peptide dissolved in 10 mM phosphate buffer pH5, 5 mM EDAC and 5 mM NHS was incubated for 30 min under gentle shaking. The resulting activated NHS-carboxyl C-terminal moiety of each peptide (15 nmoles) was used to be conjugated in each well of CovAbtest-Plate™ previously deprotonated during 15 min with 150 µl 0.6% sodium bicarbonate per well. The microtiter plate was then incubated during 2 hrs at room temperature and washed extensively with Tris Buffer Saline.

B-I-2: Preparation of Covalently Coupling Peptides to BSA (BSA-Peptide Conjugate)

2 mg of each peptide was dissolved in 1 ml of deionized water and 150 nmoles were mixed with 0.5 mg BSA solubilized in 50 mM bicarbonate buffer pH9.5. After shaking, glutaraldehyde was added at a final concentration of 0.25% (v/v). The mixtures were kept at room temperature during 16 hrs under gentle shaking. At the end of this incubation time, sodium borohydride was added at a final concentration of 10 mg/ml to stabilize the cross-linking between BSA and the peptides. After 2 hours each mixture of peptide-BSA was dialyzed separately in PBS to remove any free peptides.

B-I-3: Preparation of Covalently Coupling Peptides to IgG (IgG-Peptide Conjugate)

600 nmoles of HH12Q11 peptide solubilized in deionized water were mixed with 60 µmoles of EDAC and 60 µmoles of NHS in 0.2 M phosphate buffer pH 5 to activate the alpha carboxyl of the C-terminal amino acid. After 30 min incubation at room temperature under gentle shaking, 500 µL of the peptide solution was added to 0.5 mg of Human IgG diluted at 1 mg/ml in 0.2M phosphate buffer pH8.5. The final mixture was then incubated at room temperature during 16 hrs and under gentle shaking. Then each solution was dialyzed separately in PBS as described in M-1.

B-I-4: Preparation of Microtiter Plates Coated with BSA-Peptide & hIgG-Peptide Conjugates High binding 96 wells-microtiter plates (Costar) were used to immobilize BSA-peptide and to human IgG-peptide conjugates prepared as described in M-4 and M-5. For these experiments, conjugates were prepared at 50 µg/ml in 50 mM sodium carbonate buffer pH 9 and 100 µl of each solution was dispensed in the number of wells needed for the experiment. After overnight incubation at 4° C., the plates were washed extensively with Tris Buffer Saline (TBS) and were ready to be used for TG activity.

B-I-5: Preparation of Covalently Coupling Spermine to 96 Well-Microtiter Plates (Covabtest-Spm)

To produce the Covabtest-spm plate, the procedure previously described in Mily et al (2009) was used.

B-II-Methods for Measuring Transglutaminase Activities

B-II-1: Transglutaminase Mediated Incorporation of Biotin-X-Cadaverine into Peptides Coupled on Covabtest-Plates (B-I-1).

For this experiment we used the same procedures described by V Thomas et all (2004) and also in the Covalab's commercialized kit (opr0033). Briefly the Lyophilized transglutaminase was reconstituted in 40 mM tris buffer pH 8 and 50 µl of each mTG at 200 ng/ml and at 40 ng/ml were added in the wells containing 50 µl of biotin-X-cadaverine. The enzymatic mixture was incubated for 15 min at room temperature under gentle shaking. Then the plates were washed 3 times with TBS-Tween20 followed by the addition of 100 µl of diluted HRP labeled streptavidine (1/2000 in TBS Tween20, 0.5% BSA) in each well. After 30 min at room temperature and 3 washings in TBS-Tween20, 100 µL of TMB substrate were added and after 5 min the colour development was stopped using 100 µl of 0.5 M sulfuric acid. Absorbances at 450 nm were measured using a microplate reader (Multiskan, Labsystems, Helsinki, Finland).

B-II-2: Transglutaminase Mediated Incorporation of Biotin-X-Cadaverine into BSA-Peptide Coated Plate (B-I-2).

The same procedure was used as described in B-II-1

B-II-3: Control of the Specificity of Transglutaminase Enzymatic Reaction by Competitive Assay Using BSA-Peptide Conjugate (B-I-2).

In this experiment, peptide-1 (TGpan (table 2)) was conjugated to BSA according to the method described in B-I-2 and used to coat the 96 wells microtiter plates as described in B-I-4. Then the peptides reported in table 2 (non biotinylated peptides) were used as a putative competitors at the concentration of 600 µM in 40 mM TBS pH8. In each well the following reagents were added in duplicate: 25 µl of peptide competitors, 25 µL of mTG at 400 ng/ml and 50 µl of Biotine-X-cadaverine. After 15 min incubation at room temperature the plate was washed 3 times with TBS-Tween20 and 100 µl of HRP labeled streptavidine was added following the procedure described in the previous methods. As a negative control we used YV10 peptide which does not contain any Glu (Q) donor.

B-II-4: Screening of the Preferred Substrates for mTG

For the screening of the peptide listed in table 2 (Biotinylated peptides) the inventors used our colorimetric assay to measure transglutaminase 2 (TG2) cross linking activity (Mily et al, 2009) and commercialized under ref opr0033 in which mTG was used instead of TG2 and described in this experience. The principle of the method is based on the transamidation activity of mTG, using covalently coupled spermine to carboxy-substituted polystyrene plates and biotinylated peptides. The assay consists of the incorporation of the glutamine gamma-carboxamide group into the immobilized spermine. The amount of biotinylated peptide bound to the plate, as measured by the activity of streptavidin-peroxidase, is directly proportional to the TG activity. Absorbance was measured at 450 nm using the microplate reader.

In order to compare the affinity of mTG to the preferred substrate, the peptides were used at different concentrations ranging from 160, 80, 40, 20, 10, 5, 2.5 and 0 µM. Then the apparent Km were determined for each peptide and were calculated by Lineweaver-Burk method (1/Absorbance=f(1/[mTG (µM)]).

B-II-5: Analysis by Western Blot of the Enzymatic Incorporation of Biotin-X-Cadaverine into Human IgG by mTG 20 µg of peptide-conjugated IgG (IgG-YV10, IgG-CW9Q3 and IgG-HH12Q11) and free IgG (control) were mixed with 13 nmoles biotine-X-cadaverine and 0.6 ng mTG in a final volume of 150 µl. The reaction mixtures were incubated 2 hours at room temperature for end point experiments and 0, 10, 20 and 60 min for the kinetic study. At the end of each time, 20 µl of each solution were transferred in a tube containing 4 µl of electrophoresis loading buffer (0.3 M Tris HCl pH 6.8, 0.6 M dithiothreitol, 12% SDS, 0.6% bromophenol blue and 50% glycerol) and boiled at 90° C. during 5 min. SDS polyacrylamide gel electrophoresis in denaturizing conditions was used to separate the mTG and the different subunits of the hIgG as described by Laemmli et al, 1970. Briefly, 15 µl (1.3 µg) of each sample were loaded on 10% polyacrylamide gel and the migration was carried out during 1 hr at 100V. At the end of this period, the transfer of the proteins from the SDS-polyacrylamide gel to the Hybond Western Blot-C nitrocellulose membrane (Amersham Life Science, UK) was carried out during 1 hr at 100V using the method of Towbin et al, 1979. To detect biotin-X-cadaverine covalently coupled to hIgG, the membrane was incubated 1 hr at 37° C. in Tris buffer saline (TBS) containing 0.5% BSA, then probed with horseradish peroxydase labeled streptavidine diluted to 1/2000 in TBS, 0.5% Tween-20, 0.5% BSA. After 30 min incubation at 37° C., the membrane was washed 3 times with TBS 0.5% Tween-20 and 2 times in PBS. To detect peroxydase activity the membrane was incubated 2 min in the chemiluminescent reagent Covalight® and finally analyzed using a western blot imager. Western blot results in this study are representative of multiple determinations.

B-III-1 Recombinant Q-Peptide Tagged Antibodies

Three different Q-peptide tagged recombinant antibodies were produced. RecAb-Tag antibody is a human recombinant antiRhD1 antibody (IgG1) Sibéril S. Clin Immunol. (2006) 118:170-9; Saurabh K. Gupta, J B C; (2007); 282, 29431-29440 carring Q-peptide tag DHQ6Q7 (SEQ ID NO:7) at the carboxyl terminus of the heavy chain. D1-3-tag antibody is a human recombinant anti-lysozyme antibody (IgG2) carring Q-peptide tag (SEQ ID NO:32) at the carboxylic terminus of the heavy chain. Her2-tag antibody is a human recombinant anti-Her2 antibody (IgG2) caning Q-peptide tag (SEA ID NO:32) at the carboxylic terminus of the heavy chain. Both antibodies were produced according to Chapple S D, BMC Biotechnol. (2006) December 22; 6:49; Martin C D, BMC Biotechnol. (2006) December 7; 6:46.

B-III-2 Analysis by Western Blot of the Enzymatic Incorporation of Biotin-X-Cadaverine into Q-Peptide Tag of the Recombinant IgG by mTG 20 µg of recombinant IgG (tagged and non tagged antibodies) was mixed with 13 nmoles biotine-x-cadaverine and 0.6 ng mTG in a final volume of 150 µl. The reaction mixtures were incubated 15 min at room temperature for end point experiments and 5, 15, 60 min and over night for the kinetic study. At the end of each time, 20 µl of each solution were transferred in a tube containing 4 µl of electrophoresis loading buffer (0.3 M Tris HCl pH 6.8, 0.6 M dithiothreitol, 12% SDS, 0.6% bromophenol blue and 50% glycerol) and boiled at 90° C. during 5 min. SDS polyacrylamide gel electrophoresis and Western blot were undertaken as described in B-II-5.

B-III-3: Control of the Recombinant IgG Anti Lysozyme Immunoractivity by ELISA

1 µg/well of chicken egg lysozyme (ref L6876-1G; Sigma-Aldrich; France) diluted in 50 mM NaHCO3/Na2CO3 pH 9.5 was coated on 96 wells microtiter plates (high binding, Costar). After 16 hours of incubation at 4° C., 150 µl/well of a solution of PBS containing 0.5% BSA was added to prevent non specific binding. This solution was incubated 30 min at 37° C. and the plates were washed twice with PBS. Then, 100 µl of tagged D1-3 and non-tagged D1-3 recombinant antibodies anti lysozyme at 10, 5, 2.5, 1.25 µg/ml were incubated for 1 hour. Irrelevant human IgG (ihIgG) was use as a negative control. After 3 washing with TBS tween-20, 100 µl/well of horse radish peroxidase labeled antibody anti human IgGAM (PARIS, France) diluted at 1/1000 was incubated 30 min at 37° C. After extensive washing with TBS tween 20, peroxidase activity was measured using TMB/H2O2 substrate (Covalab, France) as described in B-II-1.

B-III-4: Control of the Recombinant IgG Anti Her 2 Immunoreactivity by ELISA 0.1 µg/well of recombinant Recombinant human ErbB-2/HER2 Protein (Biaffin Gmb, Germany) diluted in 50 mM NaHCO3/Na2CO3 pH 9.5 was coated on 96 wells microtiter plates (high binding, Costar). After 16 hours incubation at 4° C., BSA was added as describe in B-III-3. Then, 10, 5, 2.5, 1.25 µg/ml in 100 µl/well of tagged Rec-Her2 and anti lysozyme AD1-3 (as irrelevant tagged IgG) treated or not treated with mTG/biotin-x-cadaverine were incubated for 1 hour. After 3 washing with TBS tween-20, in one experiment horse radish peroxidase labeled antibody anti human IgGAM to detect the presence of the primary antibodies and in another experiment Streptavidin-HRP (1/2000 in TBS-Tween20) was added to detect biotin-x cadaverine incorporated by mTG. Then, HRP activities were measured as described in B-II-1

Results:

In all the experiments, the inventors used mTG (microbial/bacterial transglutaminase) as the target enzyme and the peptides GS12Q7 and its biotinylated derivative bGS12Q7 described by Sato et al (2001) as the standard substrate to compare the reactivity and the specificity of the new peptide substrates. Also TG2 (tissue transglutaminase) was used when appropriate to compare the enzymatic reactivity with mTG and also to control the specificity of the peptide substrates.

R-1: Screening of Preferred mTG Substrates According to the Method Described in B-II-1.

Figure 1:
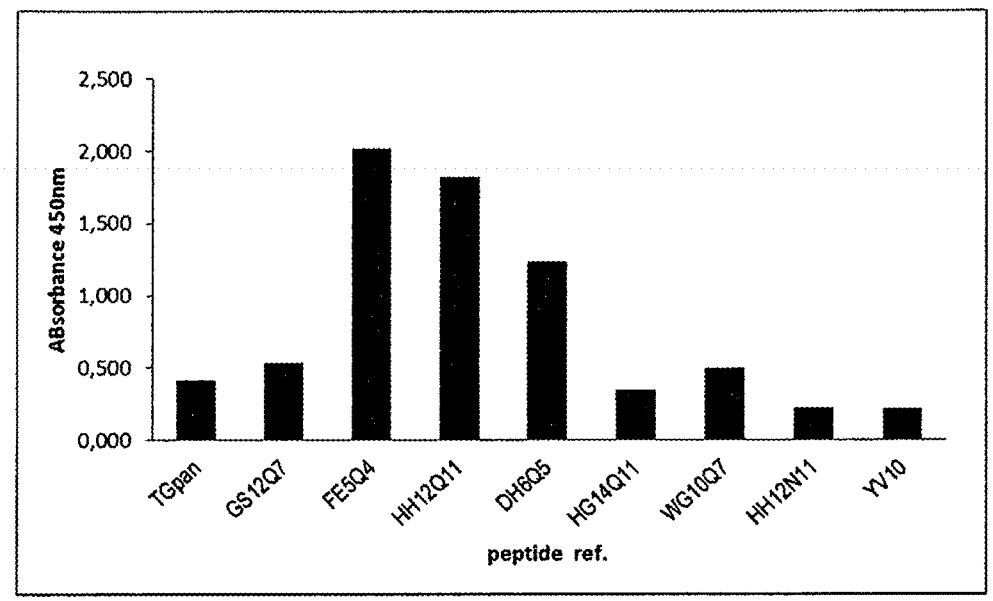
FIG. 1 shows the mTG-mediated incorporation of biotin-X-cadaverine (biot-cad) into peptides coupled on covabtest plate.

To screen the peptide library (Covalab) and identify the putative new substrates of mTG we used Covabtest-peptide (described in in B-I-1) in which the peptides were covalently coupled into the plates and the amine substrate Biotin-cadeverine (biot-cad) was free in solution. In this experiment 15 nmoles of each peptide (table 2) were covalently conjugated to microtiter plate and the incorporation of biot-cad (0.1 mg/ml) catalyzed by mTG (10 ng/well) was determined following the experiment described in B-II-1. Among all the peptides tested only few peptides were recognized by mTG as Gln (Q) donor to incorporate biot-cad as shown in the FIG. 1. The enzymatic activity was different between the peptide substrates. Peptides FE5Q4, HH12Q11 and DH6Q7 were found to be good substrate for mTG with better reactivity of the peptides FE5Q4 and HH12Q11. When Q is replaced by N (peptide HH12N11) no reactivity of the mTG was observed confirming the specificity of the enzyme to Gln donor. Moreover, if the reactivity of the 4 peptides (HH12Q11, DH6Q7, HG14Q11 and WG10Q7) is compared, it can be observed that the reactivity of the Gln depends on its position in the peptide sequence. In the most reactive peptides Q is located at the C-terminal. GS12Q7 and TGpan peptides known to be good substrates for transglutaminases showed low reactivity to mTG in comparison with the other peptides. YV10 is a negative control peptide without Q in its sequence. The other peptides listed in table 1 didn't show any reactivity with mTG.

R-2: Screening of Preferred TG2 Substrates According to the Method Described in B-II-1.

Figure 2:
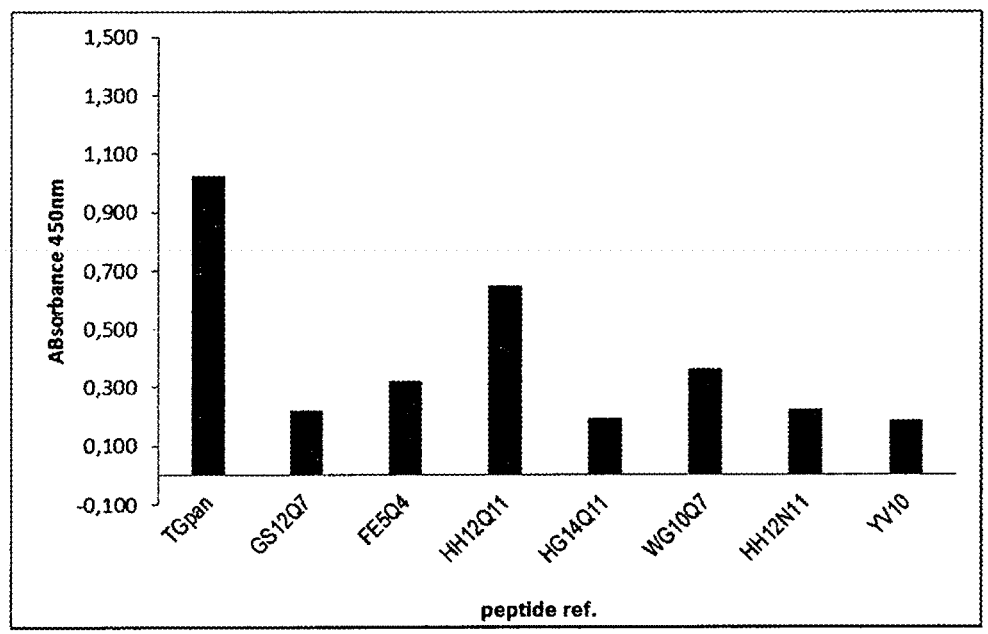
FIG. 2 shows the TG2-mediated incorporation of biotin-cadaverine into peptides coupled on covabtest plate.
Figure 3:
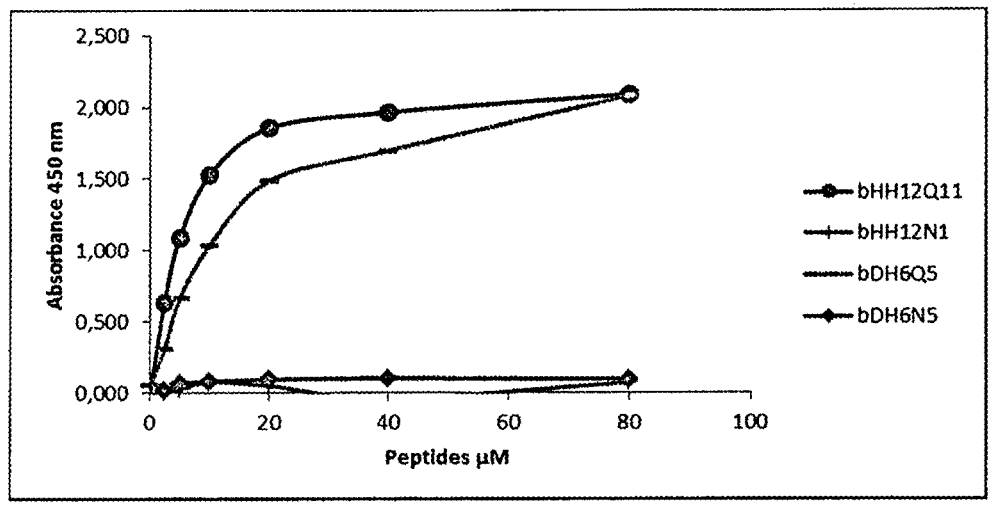
FIG. 3 shows the measurement of mTG reaction using preferred substrates and their corresponding mutated analogues at the Q residue which was replaced by N.

In a second experiment the same peptides as described above were tested using TG2 enzyme in the same conditions as for mTG. The results presented in FIG. 2 show clearly that TGpan is good substrate for TG2 confirming its specificity to this enzyme. HH12Q11 show less reactivity with TG2 than mTG. In this experimental condition none of the other peptides react with the enzyme and cannot be used as substrate for TG2. These results indicate that the position of glutamine donor and the amino acid surrounding the glutamine are important for the specificity of the enzymes.

R-3: Determination of the Affinity of the Screened Peptides

The table 3 below discloses the determination of the apparent Km of the peptide substrates of mTG ((b) biotin tagged peptide, (nr) peptide not recognized by the enzyme). Q donor is in bold and underlined. In some peptides Q was replaced by N

TABLE 3

| Peptide reference | Sequence | SEQ ID NO | $Km_{app}$ (µM) |
|---|---|---|---|
| bCV6Q3 | CHQSYV | 19 | nr |
| bPH6Q4 | PLVQSH | 20 | 14.77 |
| bHH12Q11 | HDLMWPDVYSQH | 6 | 3.08 |
| bHH12N11 | HDLMWPDVYSNH | 10 | nr |
| bWH8Q7 | WPDVYSQH | 7 | 11.40 |
| bVF7Q5 | VWRSQYF | 21 | nr |
| bDH6Q5 | DVYSQH | 1 | 33.10 |
| bDH6N5 | DVYSNH | 13 | nr |
| bDE6Q5 | DVYSQE | 22 | nr |
| bHL8Q6 | HNKSQAL | 23 | nr |
| bHP6Q3(A) | HSQALP | 3 | nr |
| bLN11Q8-10 | LLTLPSVQEQN | 24 | 172.00 |
| bLN11Q10 | LLTLPSVSEQN | 25 | nr |

TABLE 3-continued

| Peptide reference | Sequence | SEQ ID NO | $Km_{app}$ (µM) |
|---|---|---|---|
| bPS6Q3 | PSVQES | 4 | nr |
| bFE5Q4 | FWIQE | 2 | 5.00 |
| bKL7Q5 | KEEFQPL | 26 | nr |
| bSY8Q6 | SPLKHQEY | 27 | >50.00 |
| bWD7Q7 | WPLMMQD | 28 | nr |
| BEST1 | YEIQR | 29 | 0.086 |
| BEST2 | YEAQK | 30 | 0.114 |
| BEST3 | YEAQR | 31 | 0.08 |
| BEST4 | WPAQR | 32 | 0.225 |
| BEST5 | YEVQK | 33 | 0.126 |

In the experiments above, it was shown that some of the peptides were found to be good substrates of mTG. In this study, the inventors have determined the optimal sequence of the peptides containing the Gln residue which are not known to be substrate of mTG. To that end they produced several peptides in which Q was added at different position of the peptides and they varied the amino acids surrounding the Gln donor (see table 1).

In this experiment, spermine was conjugated into the plate as described in B-II-4. Biotinylated peptides described in table 3 were incubated with mTG at different concentration (160, 80, 40, 20, 10, 5, 2.5 and 0 µM). To compare the affinity of mTG to the substrates the apparent Km were determined for each peptide and were calculated by Lineweaver-Burk method (1/Absorbance=f(1/[mTG (µM)]). From table 3 it's clear that peptides HH12Q11, and its short derivatives (WH8Q7 & DH6Q5) are highly reactive with mTG. In these peptides Gln donor is surrounded by serine (at the position X−1) and histidine (at the position X+1) which are essential for the recognition by mTG. When histidine (at X+1) is changed to glutamic acid (E) in DE6Q5 the reactivity seems to be lost. The same results were obtained with PH6Q4 and PS6Q4 peptides. Even if E seems to abolish the reactivity of the peptides this cannot be due to the negative charge only but also to the nature of the amino acides at the position X+1, X+2 and X+3. Indeed, FE5Q4 peptide which has E at X+1 show high reactivity with mTG due to the environment of the amino acids at the other side of the peptide. This is confirmed with LN-11Q8Q10 peptide. For this peptide only Q at position 8 is substrate of mTG as its replacement by S in LN11Q10 inhibit completely the reactivity of the peptide.

Table 3 also shows that peptides of SEQ ID NO:29, 30, 31, 32 and 33 are excellent substrates for transglutaminases.

For the other peptides in this table no reactivity was obtained due to the position of the Gln and the surrounded amino acids.

Figure 4:
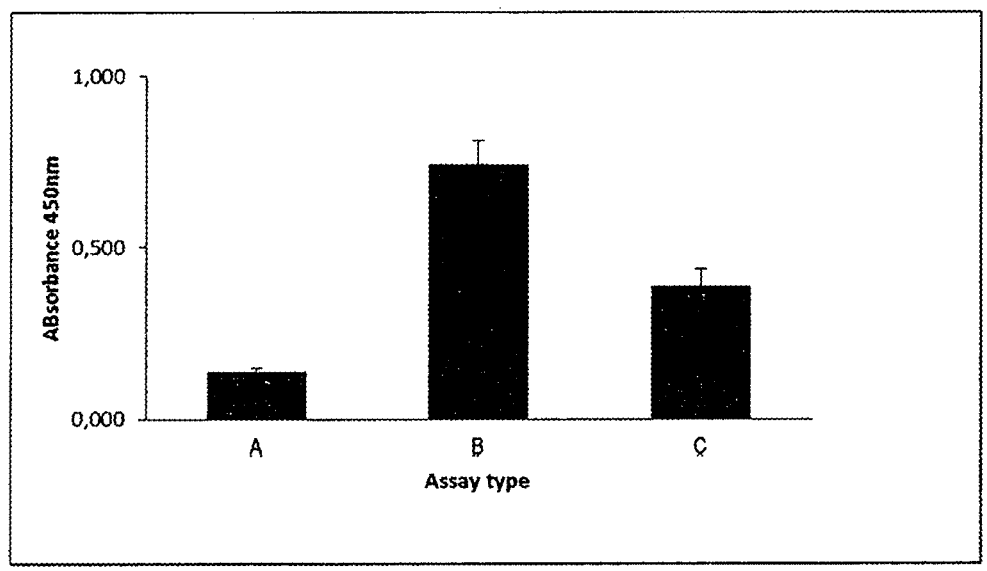
FIG. 4 shows the control of the specificity of the mTG mediated cross linking of biot-cad on BSA-HH12Q11 conjugate ((A: BSA (control well); B, C: BSA-HH12Q11).

R-4: Control of the Specificity of the Selected Peptides for mTG Enzymatic Reaction In order to confirm the specificity of mTG reaction on the highly reactive peptide HH12Q11 and its small derivatives DH6N5, the inventors have synthesized the mutated analogue peptides in which the Gln donors (Q) were replaced by asparagine (N). FIG. 4 shows the results obtained with these peptides (HH12Q11/HH12N11 and DH6Q5/DH6N5). The results are conclusive as the replacement of Q by N in these best preferred substrates of mTG abolish totally the enzyme reactivity.

R-5: BSA Conjugated with Preferred mTG Substrate Become Good Substrate of the Enzyme.

In the literature its well known that many proteins are not substrate of transglutaminase even if many glutamine residues are present in their structures (Gorman J J, Folk J E. J Biol Chem. 1984 Jul. 25; 259(14):9007-10). Bovine serum albumin (BSA) and immunoglobulins (Ig) are among these proteins. In this experiment we verified whether BSA conjugated to mTG substrate can be recognized by the enzyme. To do so, the peptide HH12Q11 was covalently conjugated to BSA as described in B-I-2. Then, 1 µg/ml of non modified BSA and BSA-HH12Q11 conjugate were coated into 96-wells microtiter plates for biot-cad incorporation by mTG. In another assay free HH12Q11 was added in the mixture reaction to analyze its inhibition effect on mTG. For clarity of this competitive assay, mTG was used at 100 ng/ml and 150 µM of free peptide and 0.1 mg/ml of biotin-cad.

The results in the FIG. 4 show that a good incorporation of biot-cad was obtained with BSA-HH12Q11 conjugate and no reactivity with free BSA, confirming that BSA is not substrate of mTG. The reactivity of mTG on BSA-HH12Q11 was decreased when the free peptide was added demonstrating the specificity of the enzyme to this peptide and confirm the results obtained in R1.

R-6: Human IgG Conjugated with Preferred mTG Substrate Become Good Substrate of the Enzyme.

In this experiment preferred substrate peptide HH12Q11 was covalently coupled to human IgG as described in B-1-2 and with its control (free IgG) they were coated (1 mg/ml) in 96-well microtiter plate as shown in B-I-4. The incorporation of biot-cad (0.1 mg/ml) was studied using different amount of mTG as shown in FIG. 5.

The results clearly show that free human IgG is not substrate of mTG and when conjugated to HH12Q11 peptide strong incorporation of the primary amine (biot-cad) was obtained. The low optical densities obtained with free IgG are equivalent to the background levels obtained without the addition of mTG.

R-7: Western Blot Analysis of the Enzymatic Incorporation of Biotin-Cadaverine into Human IgG-HH12Q11 Conjugate by mTG In order to determine whether human IgG can be used as a carrier of mTG substrate, HH12Q11 and FE5Q4 (mTG peptide substrates) and YV10 (peptide control) were conjugated to human IgG and analysed by western blot as described in B-II-5.

The results presented in FIG. 6 show that both IgG conjugated with HH12Q11 and FE5Q4 peptides were able to incorporate biotin-cadeverine after 2 hrs incubation with mTG. IgG-HH12Q11 seems to incorporate more biot-cad as indicated by the intensity of the staining. Moreover IgG-HH12Q11 has more affinity to mTG than IgG-FE5Q4 as the incorporation of the amine substrate started at the initial enzymatic reaction (T0) (arrow). Free IgG and IgG conjugated with peptide control (YV10) didn't show any staining. These results confirm our previous results mentioned in R-3.

The results of the kinetic study present in FIG. 7 show that both IgG conjugate with HH12Q11 and FE5Q4 incorporate biotin-cadeverine quickly in less than 10 minutes and this incorporation was increased during the time with high incorporation at 1 hr. Again free IgG and IgG conjugated with peptide control (YV10) didn't show any staining indicating that free IgG is not substrate of mTG.

R-8: Recombinant Tagged Antibodies

Three different antibodies containing Q-peptide tag at the extreme C-terminal domain of their heavy chain were engineered and produced in HEK-293 cells. Q-peptide (SEQ ID NO:7) was fused at the carboxylic terminus of the heavy chain of the human recombinant anti-RhD1 antibody (IgG1). In another experiment, we used Q-peptide SEQ ID NO:32 to tag and construct recombinant human anti lysozyme (D1-3) and human anti-Her2 antibodies. The tag was fused at the C-terminal of their heavy chain. Next we examined whether mTG is able to incorporate biotine-x-cadaverine into Q-peptides tagged antibodies. The results of the western blot in FIG. 10 show clear staining of the heavy chain of the antibodies tagged with SEQ ID NO:7 (FIG. 10A) and with SEQ ID NO:32 (FIGS. 10B & 10C) whereas non tagged antibodies are not stained. These findings confirm that the Q-peptide sequences are good substrates of mTG, even when they are fused in full length antibody sequences. The difference of intensity of the staining is due to the amount of the antibodies loaded in the gels.

R-9: Kinetic Study of the Incorporation of Biotin-x-Cad by mTG

Figure 11:
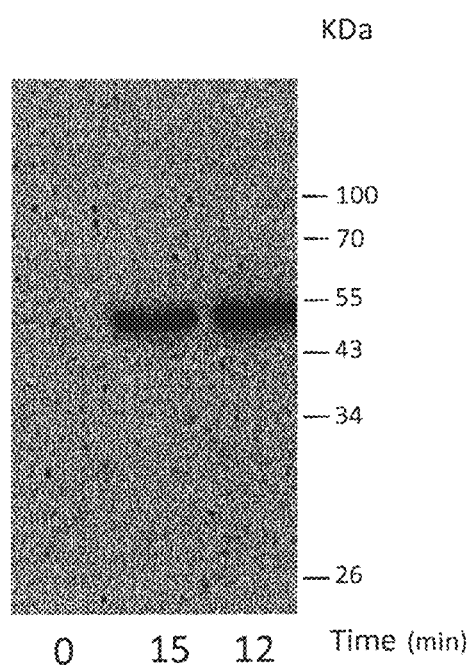

In this experiment, recombinant human anti lysozyme antibody (D1-3) tagged with SEQ ID NO:32 was incubated with mTG and biotin-x-cadaverine for 0, 15 and 120 min and the enzymatic crosslinking reaction was measured by streptavidine peroxidase as described in the material and method. The results in FIG. 11 show that the incorporation of the biotin-X-cadaverine by mTG is fast and the maximum (>50%) of the incorporation (estimated by the intensity of the signal in FIG. 11) was obtained in 15 min. This good and specific mTG reactivity confirms the results obtained with the sequences HH12Q11 and FE5Q4 shown in FIG. 7.

Figure 12A:
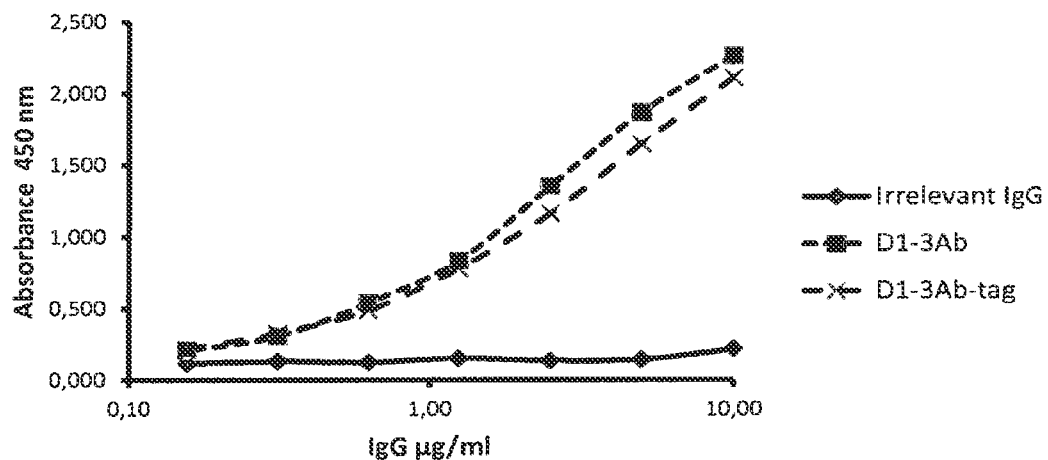
Figure 12B:
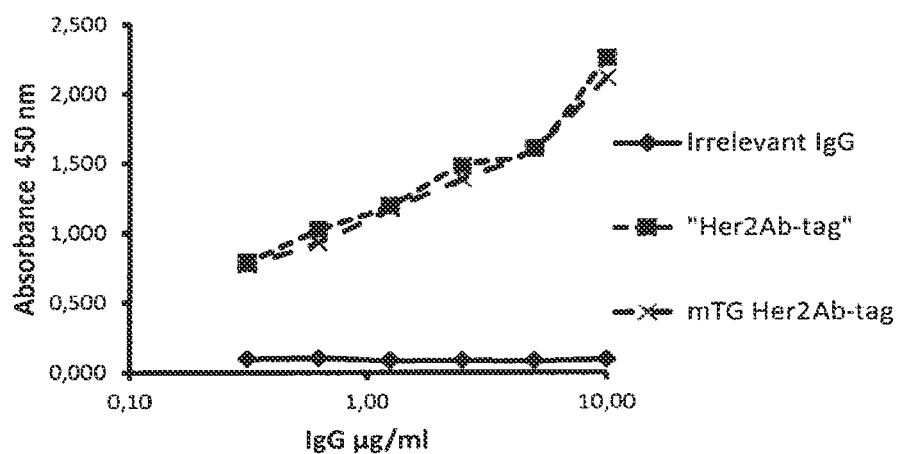
Figure 12C:
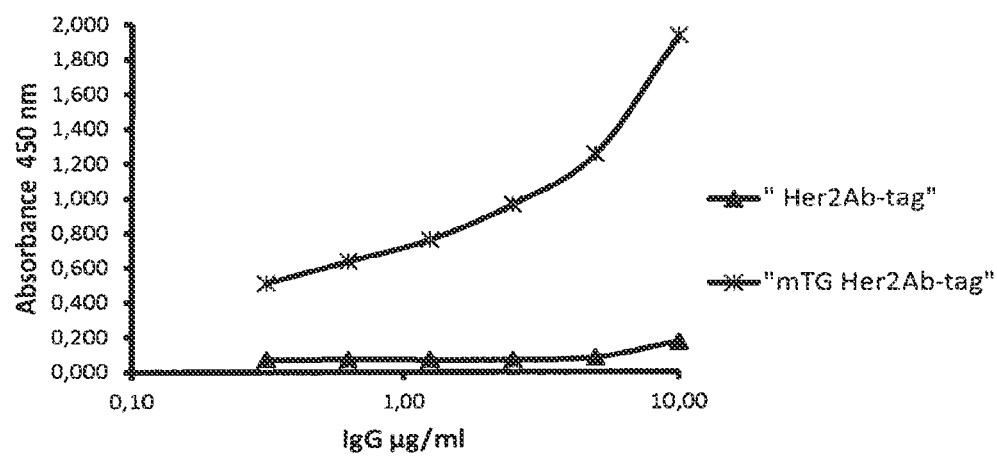

R-10: Control of the Immunoractivity of the Recombinant IgG Anti-Lysozyme and Anti-her2 by ELISA It is well known that polyhistidine and other peptides can be used to tag antibodies without any effect on their immunoreactivity. In this experiment we measured the immunoreactivity of our tagged anti-lysozyme (D1-3) and anti-Her2 antibodies on their corresponding proteins by ELISA as described in the methods B-III-3 and B-III-4. The results in FIG. 12A show clearly that tag-D1-3 has comparable immunoreactivity than the control antibody D1-3 which has no tag. hIgG was used as a negative antibody control. In FIG. 12B, the same results were obtained with tagged anti-Her2 in comparison with its non-tagged antibody. In FIG. 12C, we confirmed the stability of the immunoreactivity of the anti-HER2 antibody when conjugated to X-biotin cadaverine, via mTG. The control of the ELISA test was made using tagged and non tagged anti-lysozyme. From these experiments we confirm that the addition of small peptide sequence as substrate of mTG at the C-terminus of the heavy chain of the antibodies have no effect on their immunoreactivity.

REFERENCES

Throughout this application, various references describe the state of the art to which this invention pertains.

Perez Alea Mily, Kitamura M, Martin G, Thomas V, Hitomi K, and El Alaoui S, (2009) Anal. Biochem., 389, 150-156.

Thomas V, El Alaoui S, Massignon D, Clment S, Simonet F, Quash G. (2006) Biotechnol. Appl. Biochem., 43(Pt 3): 171-179.

Bayer E A and Wilchek M (1980) Meth. Biochem Anal., 26: 1-45.

Sugimura Y, Yokoyama K, Nio N, Maki M, Hitomi K. (2008) Arch Biochem Biophys., 477(2):379-83.

Sato H, Hayashi E, Yamada N, Yatagai M, Takahara Y. (2001) Bioconjug. Chem., 12(5): 701-710.

Laemmli, E K. (1970) Nature, 227: 680-685.

Towbin H, Staehelin T, and Gordon J. (1979) Proc. Natl. Acad. Sci., 76: 4350-4354.

FOLK J E, COLE P W. J Biol Chem. 1965 July; 240:2951-60

Gentile V., Saydak M., Chiocca E. A., Akande O., Birckbichler P. J., Lee K. N., Stein J. P., Davies P. J. A. J. Biol. Chem. 266:478-483(1991)

Ando H, Adachi M, Umeda K, Matsuura A, Nonaka M, Uchio R, Tanaka H, Motoki M: Agric Biol Chem 1989; 53:2613-2617

Sibéril S, de Romeuf C, et al. Clin Immunol. 2006 February-March; 118(2-3):170-9

Saurabh K. Gupta, et al; Journal of Biological Chemistry, 2007; 282, 29431-29440.

Chapple S D, Crofts A M, Shadbolt S P, McCafferty J, Dyson M R. BMC Biotechnol. 2006 Dec. 22; 6:49.

Martin C D, Rojas G, et al; BMC Biotechnol. 2006 Dec. 7; 6:46.

The invention claimed is:

1. A substrate for transglutaminase, consisting of:
   a peptide of 5 to no more than 15 amino acids, said peptide including the amino acid sequence selected from the group consisting of SEQ ID NO: 30, SEQ ID NO:31, SEQ ID NO:32 and SEQ ID NO:33; and
   a first molecule covalently bonded to the peptide and selected from the group consisting of an antibody, a domain antibody, a nanobody and an antigen-binding portion of an antibody.

2. The substrate for transglutaminase according to claim 1, wherein the peptide includes the amino acid sequence selected from the group consisting of SEQ ID NO: 30, SEQ ID NO:32 and SEQ ID NO:33.

3. A conjugated compound comprising the substrate for transglutaminase according to claim 1 covalently bonded to a second molecule comprising at least an alkylamine or a lysine residue.

4. The conjugated compound according to claim 3 wherein the second molecule is selected from the group consisting of a protein, an antibody, a drug, a nucleic acid, a radioactive element, a reporter group, a stabilizing molecule, an aptamer, a ribozyme, a domain antibody, a nanobody, a non immunoglobulin scaffold, a vector particle and a molecule immobilized on a solid support.

5. The conjugated compound according to claim 3 wherein the first molecule is an antibody and the second molecule is a drug.

6. The conjugated compound according to claim 5, wherein the second molecule is a cytotoxic drug.

7. A method for covalently binding the transglutaminase substrate according to claim 1, to a second molecule comprising at least an alkylamine or a lysine residue, said method comprising the step of:
   reacting the transglutaminase substrate with the second molecule in the presence of a transglutaminase.

8. The method of claim 7, wherein said transglutaminase is a bacterial transglutaminase.

9. The method of claim 8, wherein said bacterial transglutaminase is *Streptoverticillium mobaraense* transglutaminase (mTG).

\* \* \* \* \*